(12) United States Patent
Amemiya et al.

(10) Patent No.: US 10,914,804 B2
(45) Date of Patent: Feb. 9, 2021

(54) MEDICAL IMAGE DIAGNOSTIC ASSISTANCE DEVICE AND MAGNETIC RESONANCE IMAGING DEVICE

(71) Applicant: HITACHI, LTD., Tokyo (JP)

(72) Inventors: Tomoki Amemiya, Tokyo (JP); Suguru Yokosawa, Tokyo (JP); Yo Taniguchi, Tokyo (JP); Hisaaki Ochi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 420 days.

(21) Appl. No.: 15/759,112

(22) PCT Filed: Feb. 5, 2016

(86) PCT No.: PCT/JP2016/053575
§ 371 (c)(1),
(2) Date: Mar. 9, 2018

(87) PCT Pub. No.: WO2017/134830
PCT Pub. Date: Aug. 10, 2017

(65) Prior Publication Data
US 2018/0284208 A1    Oct. 4, 2018

(51) Int. Cl.
*G01R 33/56*    (2006.01)
*A61B 5/055*    (2006.01)
(Continued)

(52) U.S. Cl.
CPC ........ *G01R 33/5608* (2013.01); *A61B 5/0263* (2013.01); *A61B 5/055* (2013.01);
(Continued)

(58) Field of Classification Search
CPC .......... G01R 33/5608; G01R 33/56341; G01R 33/56; G01R 33/54; G01R 33/50;
(Continued)

(56) References Cited

U.S. PATENT DOCUMENTS 4,876,509 A * 10/1989 Perlmutter ............. G01R 33/56
324/309
5,425,368 A * 6/1995 Brandt ................... G01R 33/56
600/408
(Continued)

FOREIGN PATENT DOCUMENTS

JP    2005-118510 A    5/2005
JP    2009-61170 A    3/2009
(Continued)

OTHER PUBLICATIONS

International Preliminary Report on Patentability for International Application No. PCT/JP2016/053575, dated Aug. 16, 2018; 6 pages.

*Primary Examiner* — Oommen Jacob
(74) *Attorney, Agent, or Firm* — Procopio, Cory, Hargreaves & Savitch LLP

(57) ABSTRACT

A medical image diagnosis supporting apparatus includes a quantitative value reception unit that receives data of kinds of quantitative values obtained in advance at points in a region of a subject; a variable conversion unit that calculates kinds of intermediate information values dependent on the kinds of quantitative values at each of the points using the kinds of quantitative values at each of the points and kinds of variable conversion functions; and a diagnosis image calculation unit that calculates a diagnosis image for the region. The diagnosis image calculation unit sets a pixel value at each of the points in accordance with a combination of kinds of intermediate information values obtained at each of the points by the variable conversion unit or a combination of intermediate information values and kinds of quantitative values at the point and generates the diagnosis image.

13 Claims, 15 Drawing Sheets

(51) Int. Cl.
*G06T 11/00* (2006.01)
*A61B 5/026* (2006.01)
*G06T 3/40* (2006.01)
*G06T 5/40* (2006.01)
*G01R 33/50* (2006.01)
*G01R 33/563* (2006.01)

(52) U.S. Cl.
CPC ............... *G06T 3/40* (2013.01); *G06T 5/40* (2013.01); *G06T 11/00* (2013.01); *A61B 2576/00* (2013.01); *G01R 33/50* (2013.01); *G01R 33/56341* (2013.01); *G06T 2207/10088* (2013.01)

(58) Field of Classification Search
CPC ... G06T 11/00; G06T 3/40; G06T 5/40; G06T 2207/10088; G06T 7/0012; A61B 5/0263; A61B 5/055; A61B 2576/00; A61B 5/7235; A61B 6/00; A61B 5/02007; G06K 9/6212
See application file for complete search history.

(56) References Cited

U.S. PATENT DOCUMENTS

| | | | | |
|---|---|---|---|---|
| 7,164,808 | B2 * | 1/2007 | Srinivasa | G06T 5/008 382/274 |
| 8,150,202 | B2 * | 4/2012 | Mohanty | G06T 5/009 382/274 |
| 8,289,329 | B2 | 10/2012 | Warntjes | |
| 8,873,822 | B2 | 10/2014 | Warntjes | |
| 8,874,189 | B2 | 10/2014 | Warntjes | |
| 9,547,942 | B2 | 1/2017 | Voigt et al. | |
| 2002/0188190 | A1 * | 12/2002 | Kassai | G01R 33/5673 600/410 |
| 2004/0013292 | A1 * | 1/2004 | Raunig | G06T 7/0012 382/128 |
| 2004/0042676 | A1 * | 3/2004 | Srinivasa | G06T 5/008 382/254 |
| 2004/0169512 | A1 * | 9/2004 | Jara | G01R 33/56 324/309 |
| 2005/0043614 | A1 * | 2/2005 | Huizenga | C23F 11/08 600/427 |
| 2009/0279757 | A1 * | 11/2009 | Drabycz | G06T 7/0016 382/128 |
| 2010/0127704 | A1 | 5/2010 | Warntjes | |
| 2010/0215239 | A1 * | 8/2010 | Assaf | A61B 5/4064 382/131 |
| 2011/0288400 | A1 * | 11/2011 | Russell | A61B 5/0035 600/411 |
| 2012/0130226 | A1 * | 5/2012 | Huizenga | G06K 9/6212 600/411 |
| 2013/0281825 | A1 * | 10/2013 | Thiruvenkadam | A61B 6/5247 600/411 |
| 2014/0180061 | A1 | 6/2014 | Warntjes | |
| 2016/0055304 | A1 * | 2/2016 | Russell | G06F 19/3481 705/3 |
| 2016/0065864 | A1 * | 3/2016 | Guissin | G06T 5/50 348/239 |
| 2017/0018080 | A1 | 1/2017 | Yokosawa et al. | |
| 2018/0284208 | A1 * | 10/2018 | Amemiya | G06T 11/00 |
| 2020/0234472 | A1 * | 7/2020 | Blackledge | G06T 7/0012 |

FOREIGN PATENT DOCUMENTS

| | | |
|---|---|---|
| JP | 2011-24926 A | 2/2011 |
| JP | 2013-539706 A | 10/2013 |
| JP | 2015-510412 A | 4/2015 |
| WO | 2015/162694 A1 | 10/2015 |

\* cited by examiner

[Fig. 1]
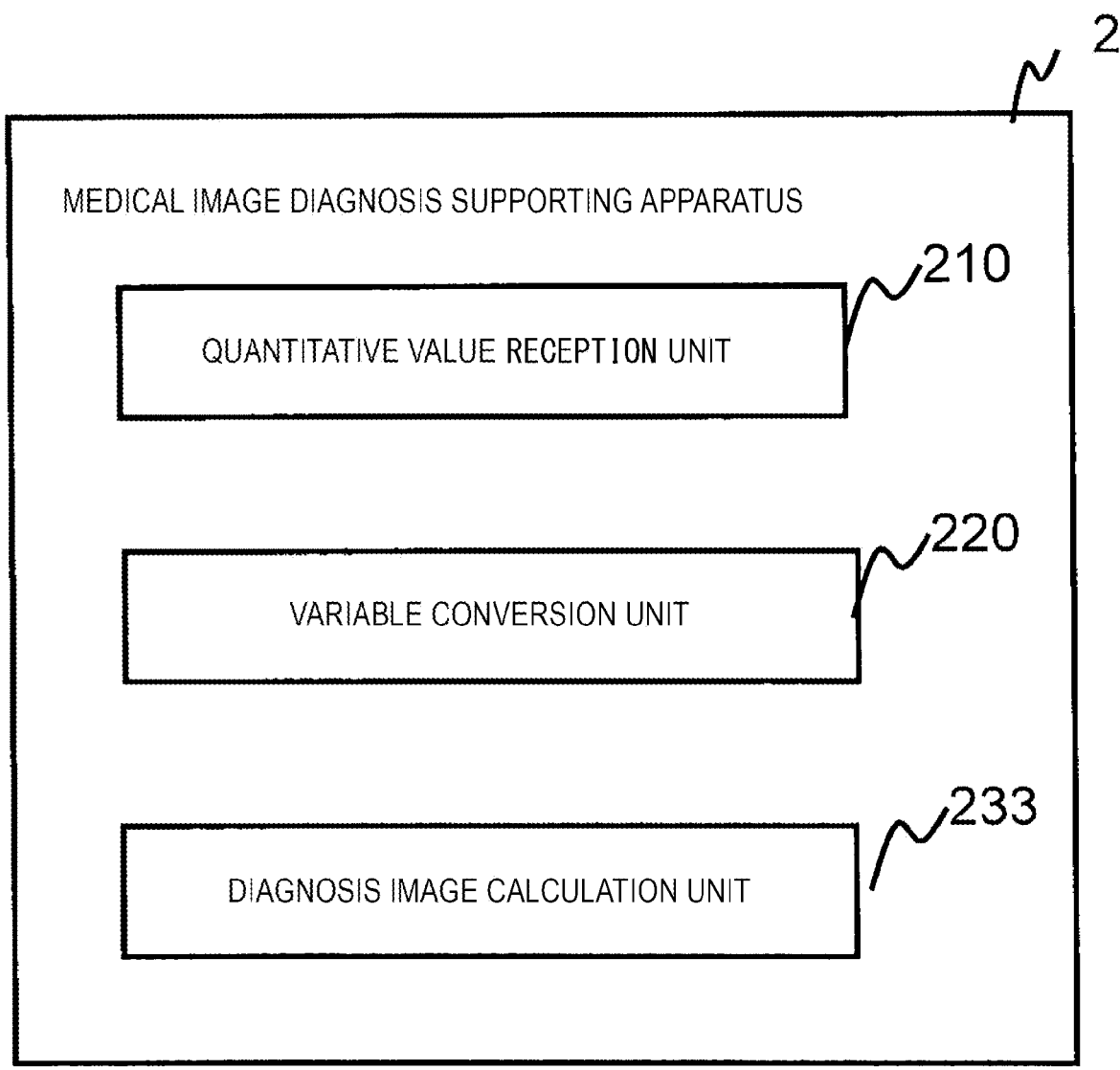

[Fig. 2]
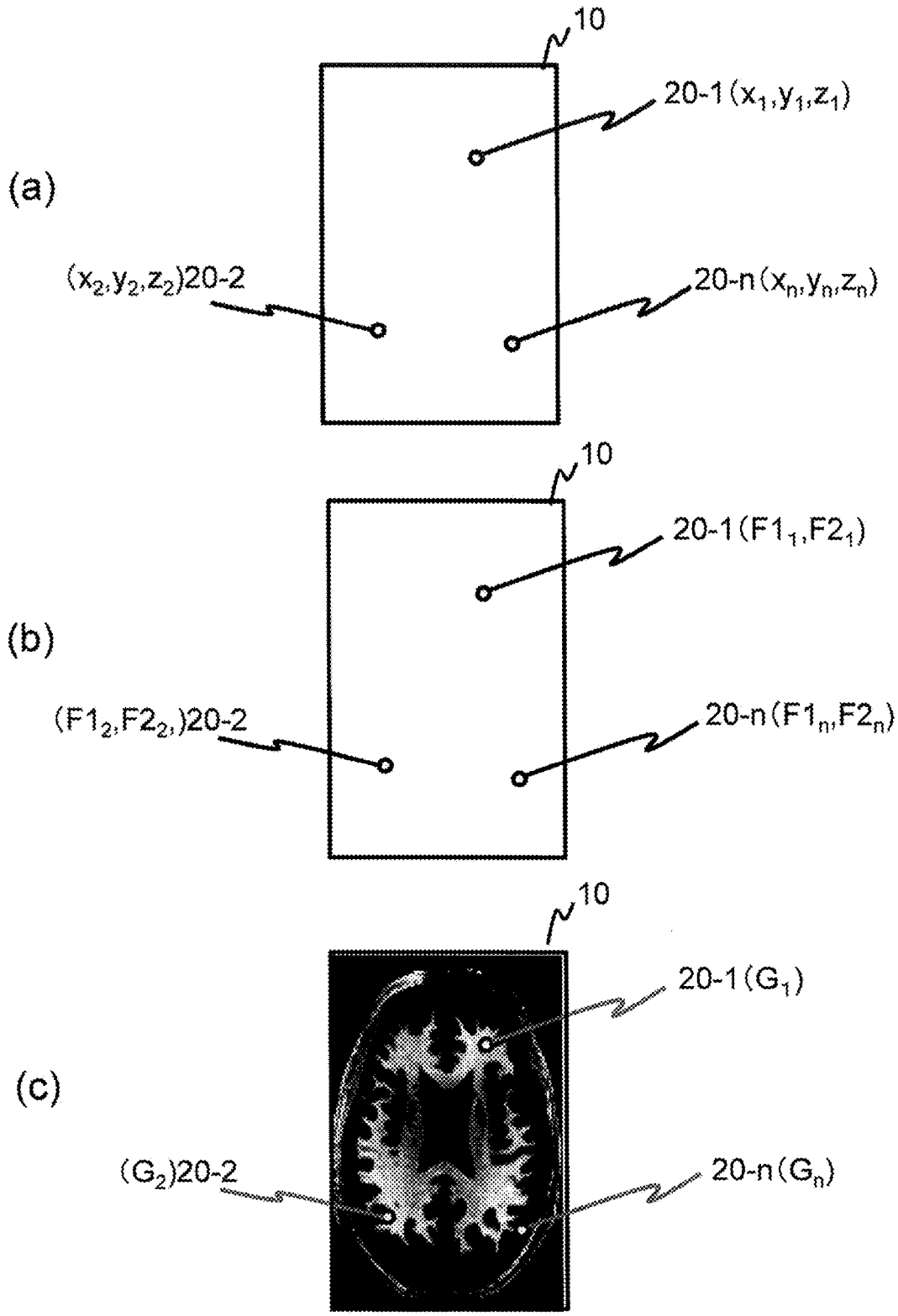

[Fig. 3]
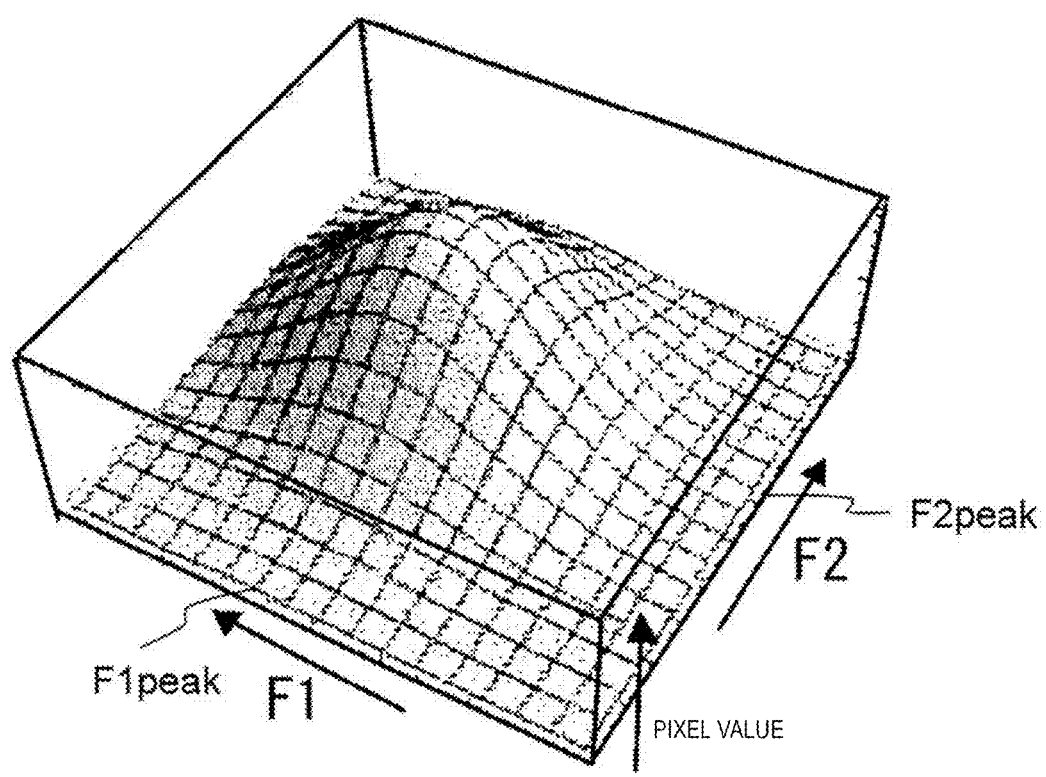

[Fig. 4]
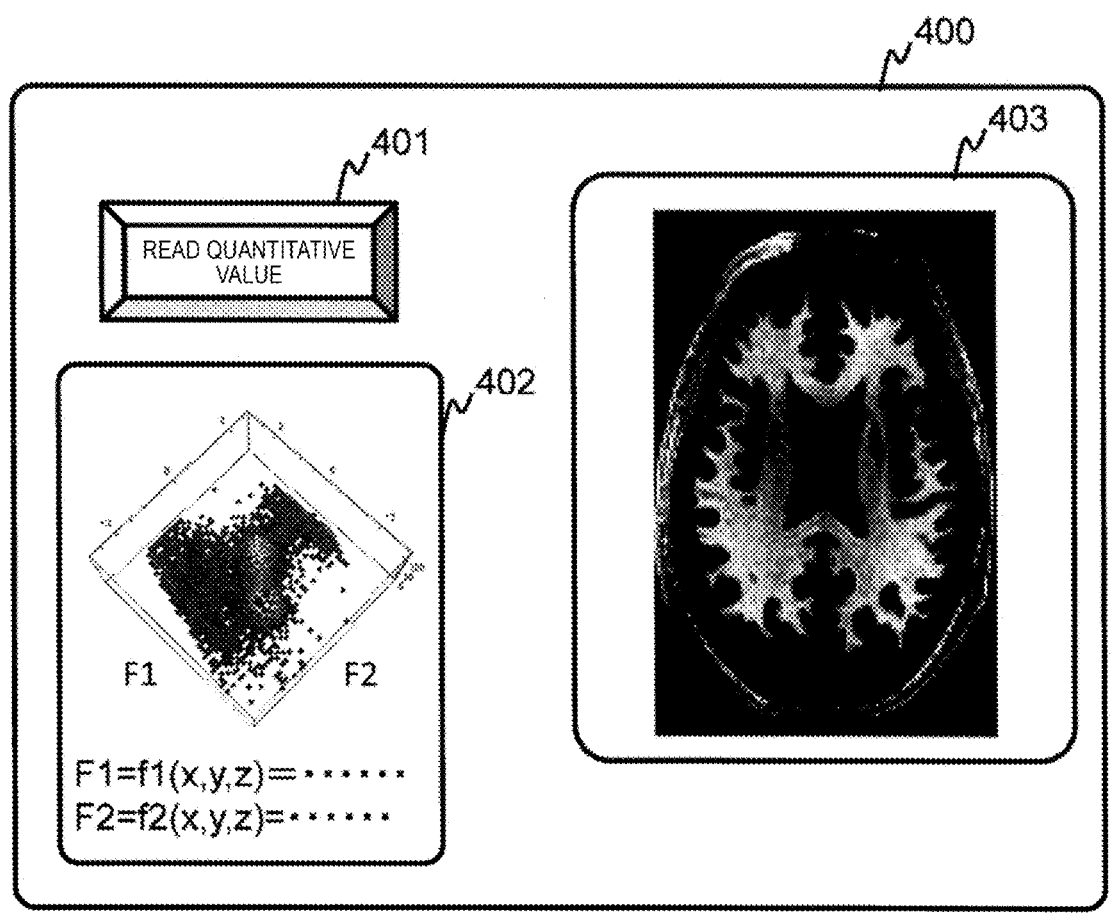

[Fig. 5]
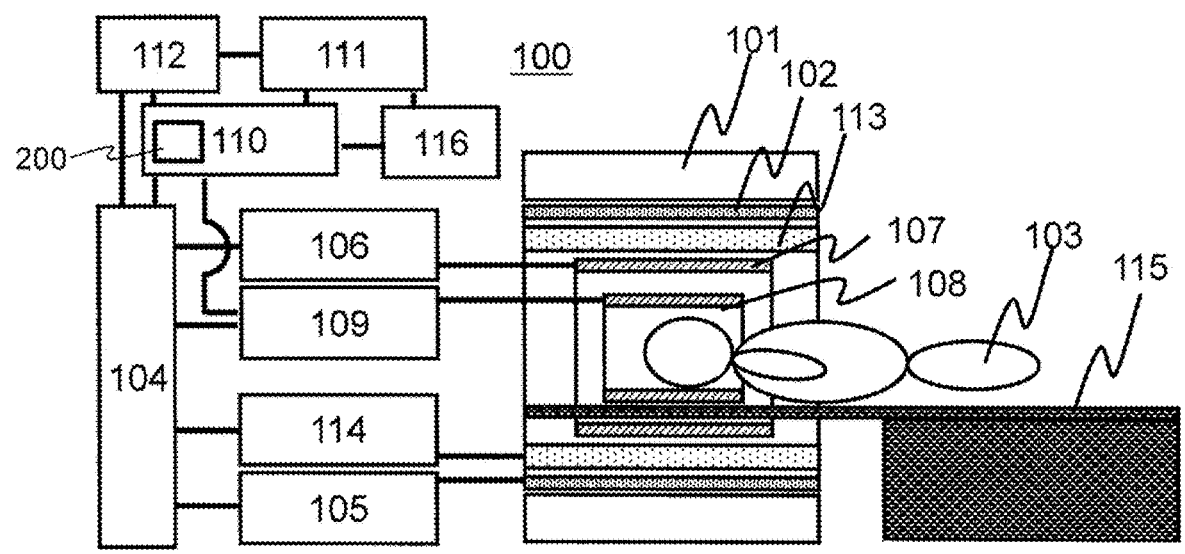

[Fig. 6]
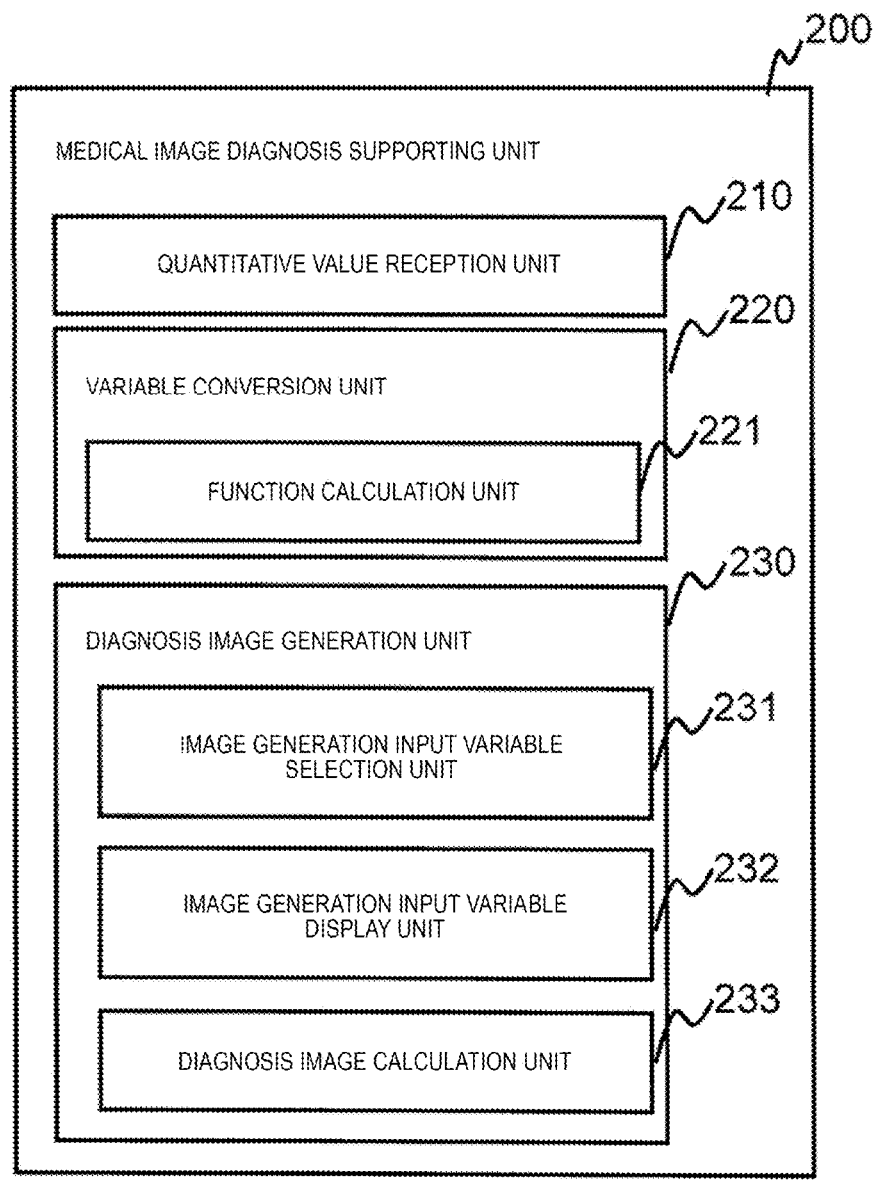

[Fig. 7]
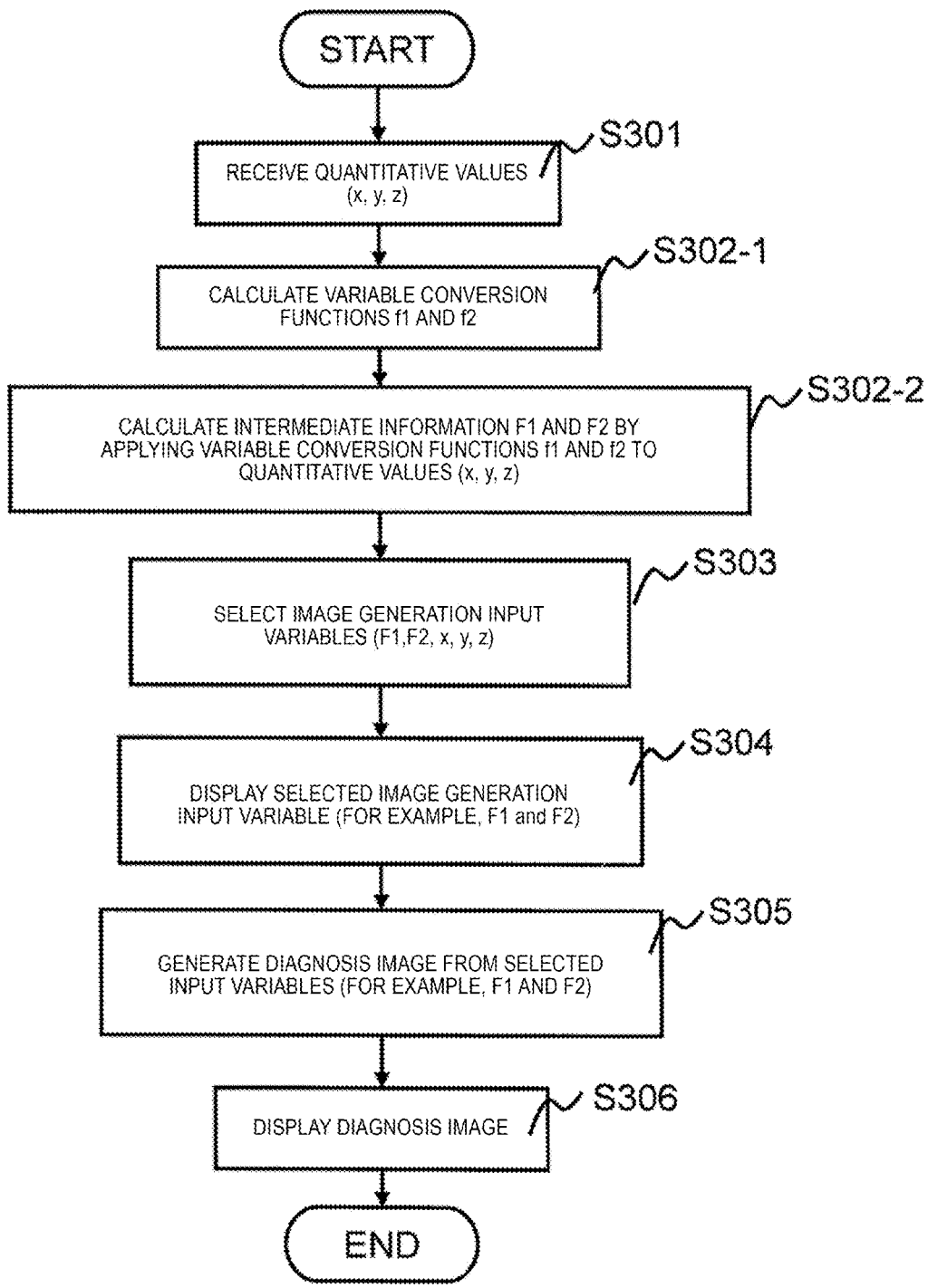

[Fig. 8]
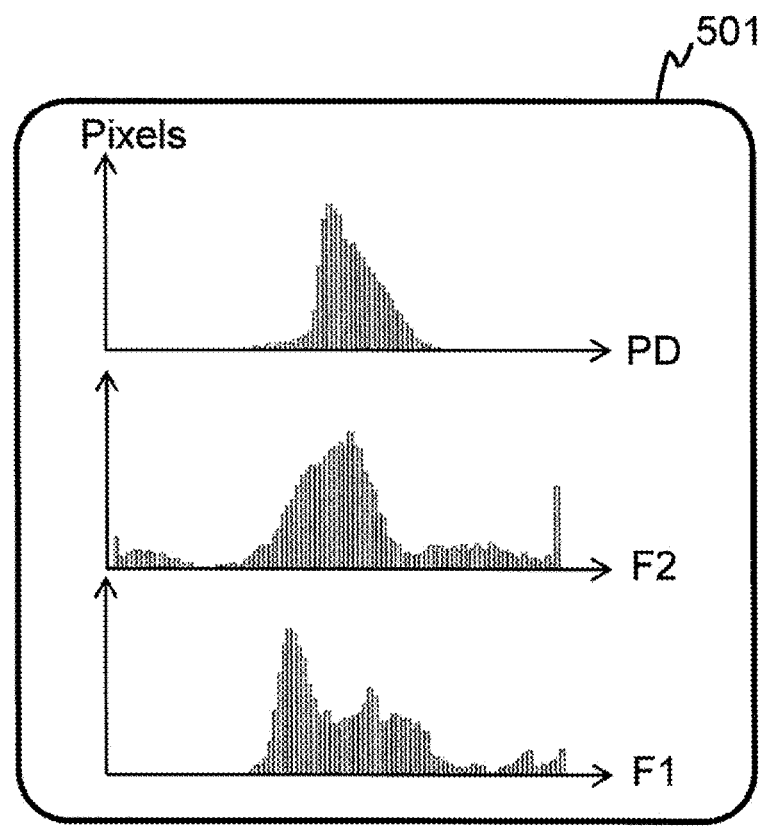

[Fig. 9]
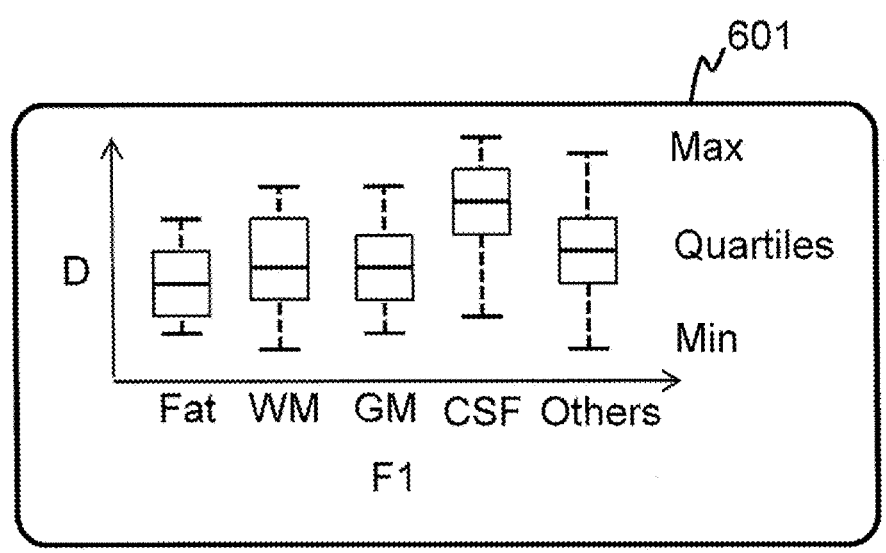

[Fig. 10]
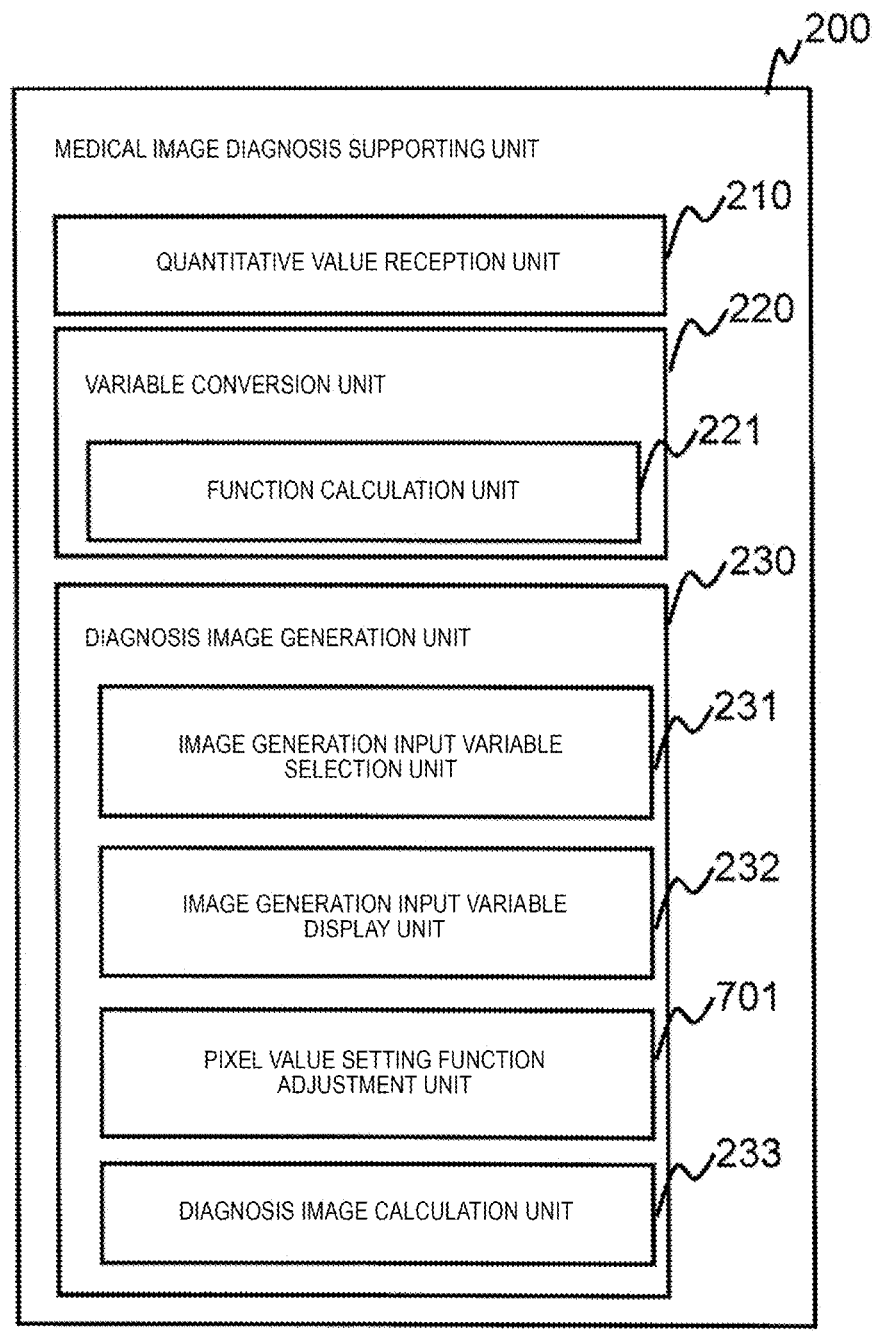

[Fig. 11]
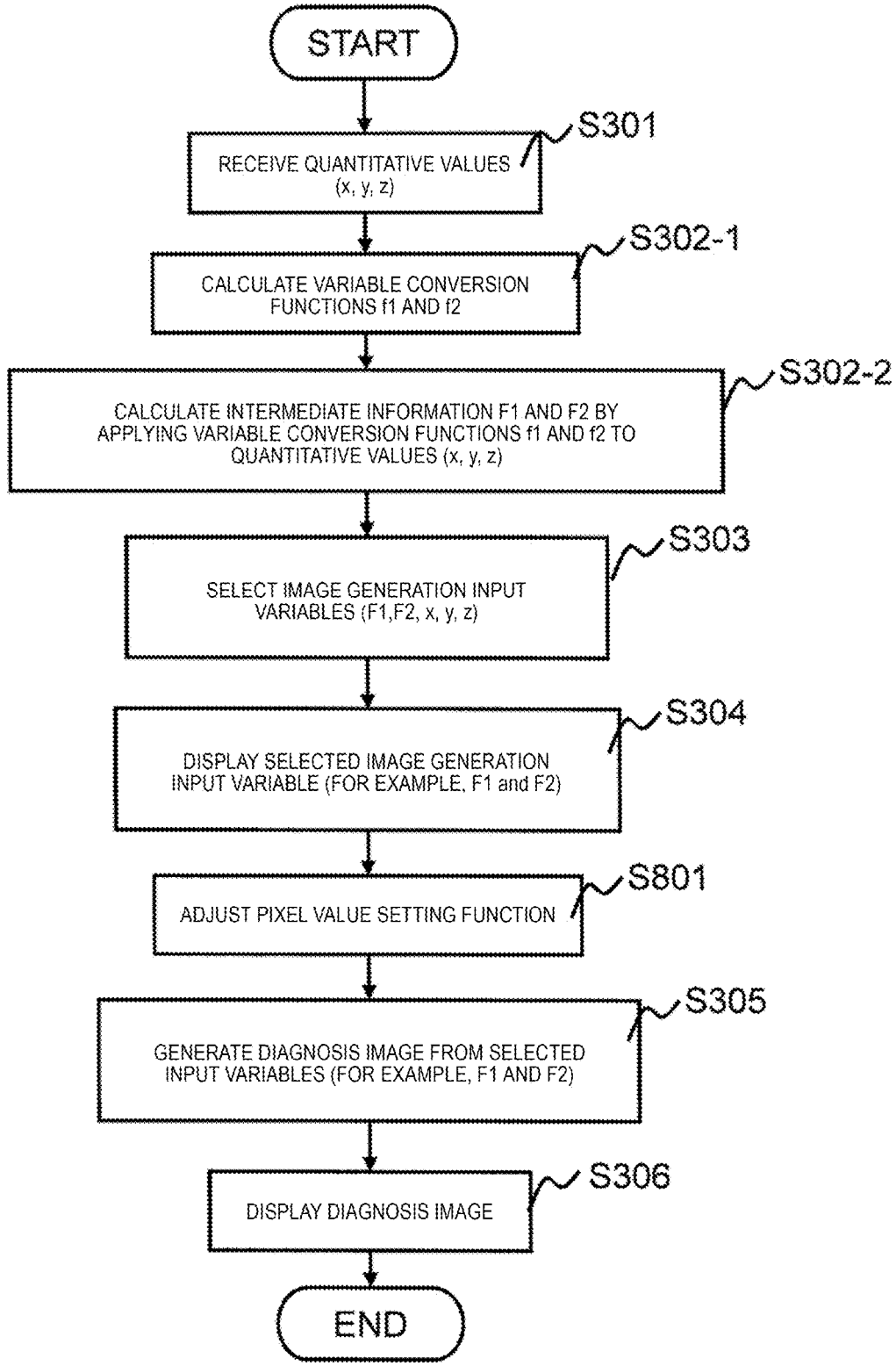

[Fig. 12]
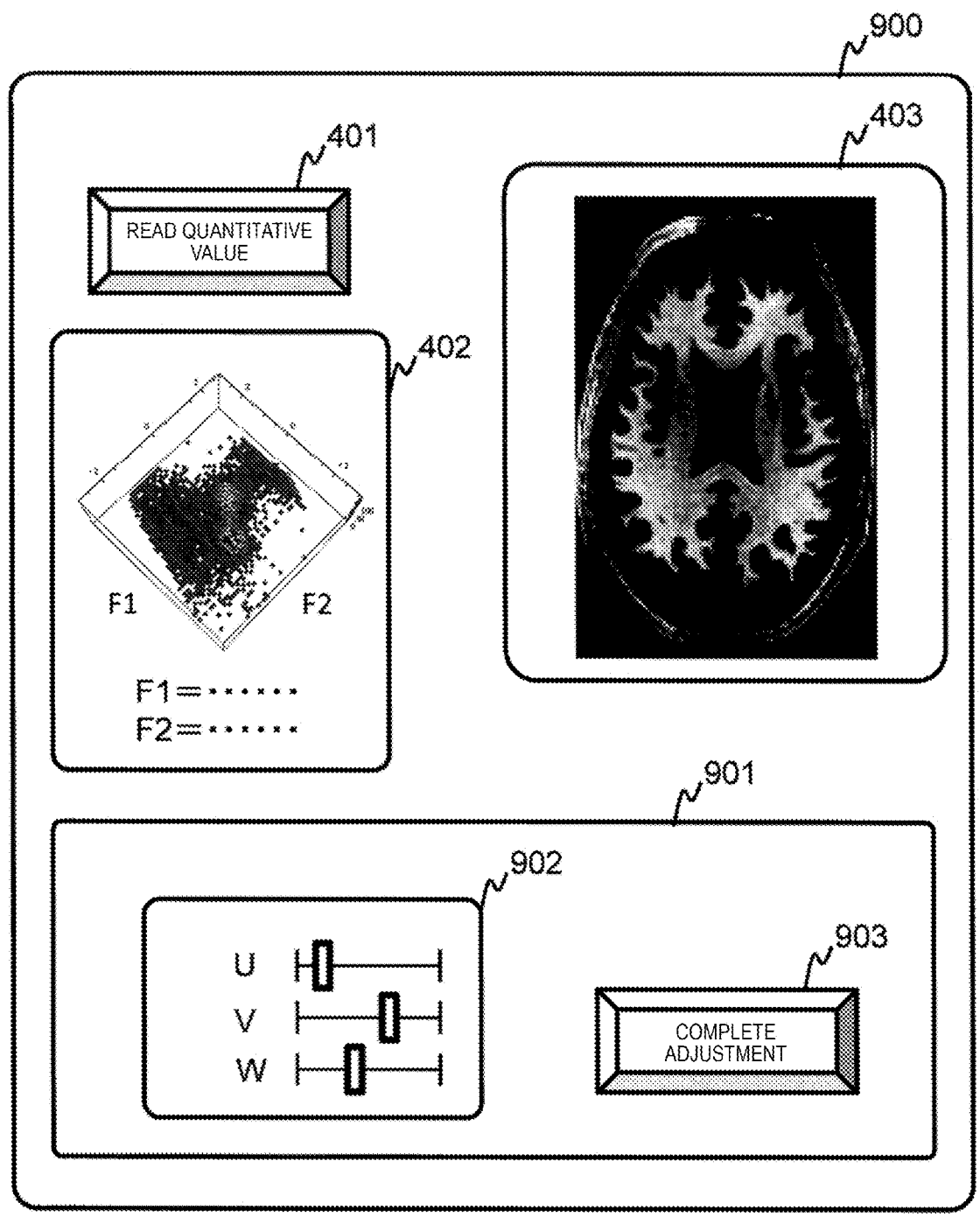

[Fig. 13]
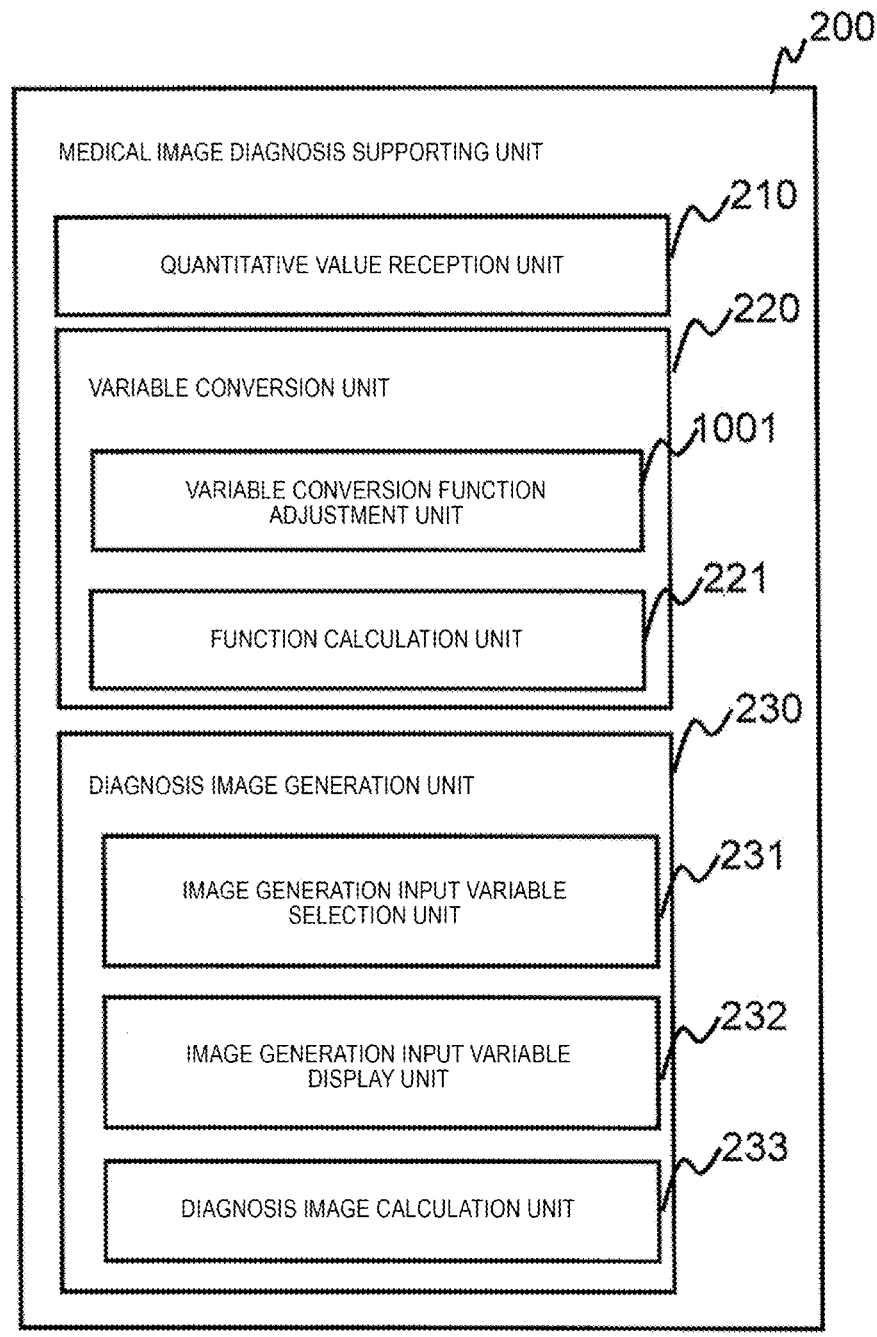

[Fig. 14]
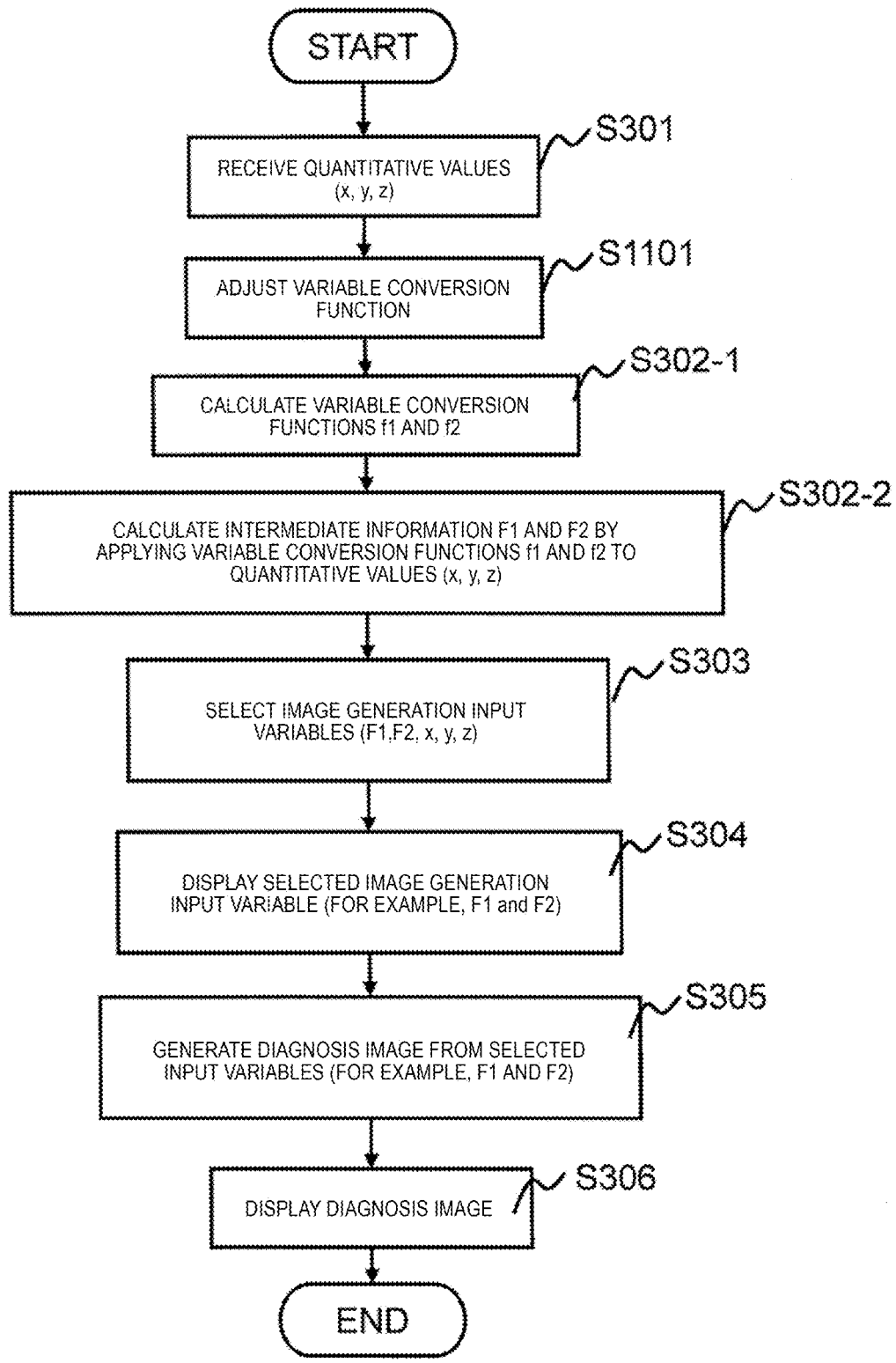

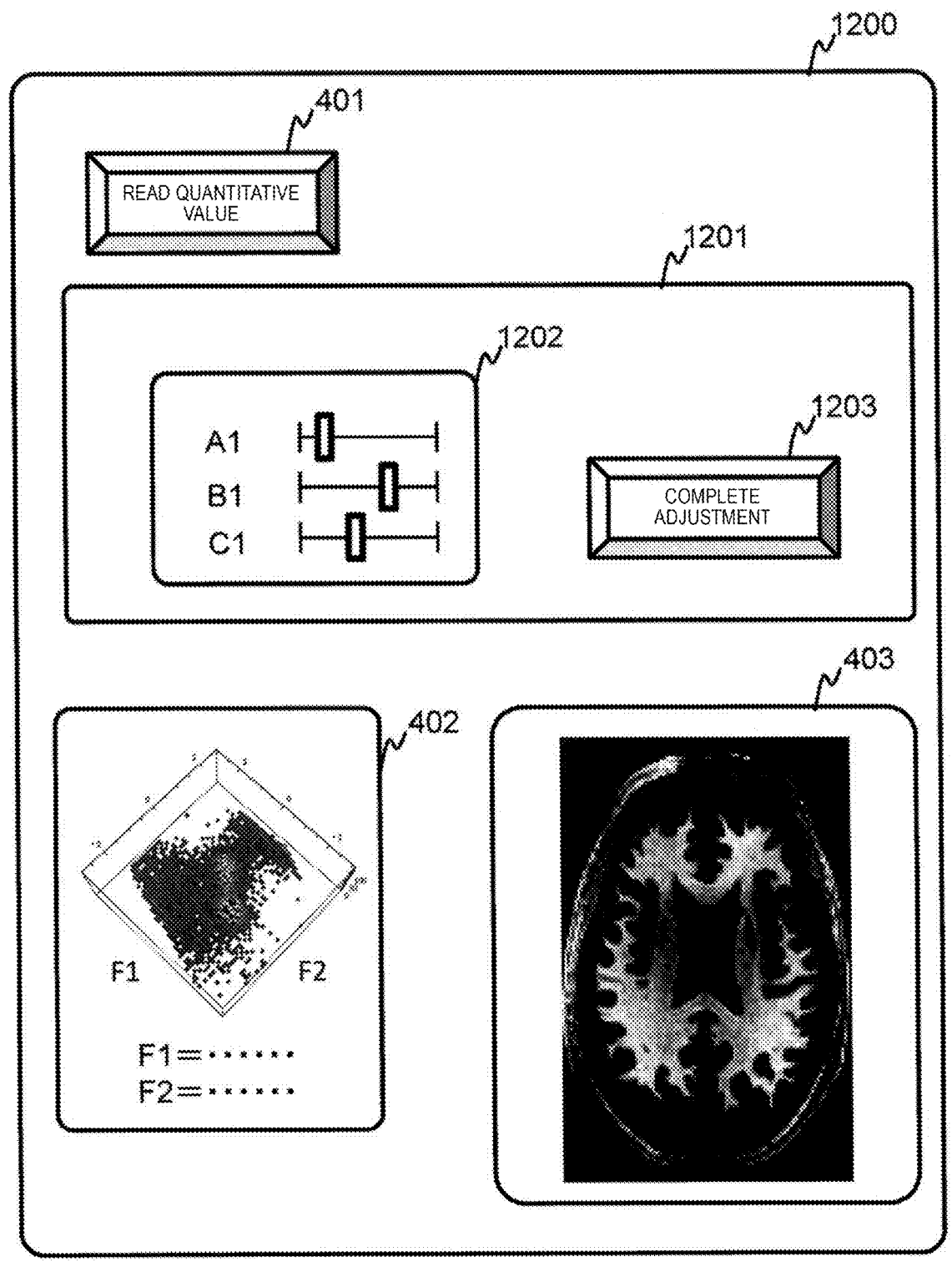
[Fig. 15]

MEDICAL IMAGE DIAGNOSTIC ASSISTANCE DEVICE AND MAGNETIC RESONANCE IMAGING DEVICE

TECHNICAL FIELD

The present invention relates to a medical image diagnosis supporting technology in which measurement data obtained by a medical image acquisition device is used.

BACKGROUND ART

There are medical image acquisition apparatuses, such as magnetic resonance imaging (hereinafter referred to as an MRI), a computed tomography (CT) apparatus, and an ultrasonic diagnosis apparatus, that obtain anatomical cross-sectional images or the like of human bodies in a noninvasive manner. In such apparatuses, images obtained by calculating acquired measurement data are displayed as diagnosis images on display devices attached to the apparatuses or display devices independent from the apparatuses.

For example, MRI apparatuses are medical image diagnostic apparatuses in which a nuclear magnetic resonance phenomenon of proton is mainly used. MRI apparatuses can image any cross section of a subject in a noninvasive manner and can acquire information regarding biological functions such as a blood flow and metabolism in addition to morphological information. In general, nuclear magnetization in a cross section desired to be imaged is excited by applying a slice gradient magnetic field to a subject placed inside a static magnetic field and simultaneously applying a high-frequency magnetic field pulse (hereinafter referred to as a RF pulse) with a specific frequency. By applying a phase encode gradient magnetic field and a read-out gradient magnetic field to the excited nuclear magnetization, planar positional information is given to measure a nuclear magnetic resonance signal (echo) in which nuclear magnetization is generated. The nuclear magnetic resonance signal is repeatedly measured until a measurement space called a k space is charged. A signal charged in the k space is imaged through inverse Fourier transform. A pulse and each gradient magnetic field for generating an echo are applied based on a pulse sequence set in advance. Various pulse sequences are known according to purposes. Imaging a subject image using an MRI apparatus is also called a magnetic resonance (MR) examination. An obtained image is also called an MR image.

In the MR examination, when a user selects and performs a pulse sequence, it is possible to acquire a weighted image in which a relative difference such as physical properties (for example, T1: longitudinal relaxation time, T2: transverse relaxation time, PD: proton density, D: diffusion coefficient, $\chi$: magnetic susceptibility, v: flow rate, and Cs: chemical shift) of a biological tissue is weighted. When the weighted degree or the physical property of a target is changed, another pulse sequence is selected or an imaging parameter is changed.

The physical properties of a subject (a biological tissue) can also be quantitatively calculated by calculation using an image obtained in accordance with a specific pulse sequence. For example, a longitudinal relaxation time T1 at each point (each pixel) in a subject can be obtained by performing imaging a plurality of times by changing an inversion time TI using a pulse sequence called an inversion recovery (IR) method. A signal intensity S at each pixel in an image obtained by the IR method can be approximated with Expression (1).

$$S(T1, B1, K1, TI, FA) = K1 \cdot \left\{1 - (1 - \cos[B1 \cdot FA])\text{Exp}\left[-\frac{TI}{T1}\right]\right\} \quad (1)$$

In Expression (1), FA is a flip angle and can be set as an imaging parameter. K1 is a coefficient determined in accordance with the proton density PD and sensitivity of a reception coil or a constant inherent in the apparatus. B1 is a radiation intensity (RF radiation intensity) of an RF pulse expressed at a ratio of the flip angle FA and is a physical amount determined in accordance with the apparatus and the subject. In Expression (1), unknown variables are three variables of the coefficient E1, the RF radiation intensity B1, and the longitudinal relaxation time T1. Therefore, by fixing the flip angle FA, performing imaging while changing the inversion time TI in three or more ways, obtaining a plurality of signal intensities 5, and estimating K1, T1, and B1 by the least squares method or the like so that an error between the function of Expression (1) and the measured signal intensity S is the minimum, it is possible to quantitatively calculate the longitudinal relaxation time T1.

Subsequently, the transverse relaxation time T2 can be obtained by performing imaging a plurality of times, while changing an echo time TE, using a pulse sequence called a spin echo (hereinafter referred to as SE) method. The signal intensity S at each pixel in an image obtained by the SE method can be approximated with Expression (2).

$$S(T2, K2, TE) = K2 \cdot \text{Exp}\left[-\frac{TE}{T2}\right] \quad (2)$$

In Expression (2), K2 is a coefficient determined in accordance with the proton density PD and sensitivity of the reception coil or a constant inherent in the apparatus. However, K2 is different from K1 in Expression (1) since a pulse sequence is different. In Expression (2), since unknown variables are two variables of the transverse relaxation time T2 and the coefficient K2, the plurality of signal intensities S are obtained by performing imaging while changing the echo time TE in two or more ways. By estimating K2 and T2 by the least squares method or the like so that an error between the function of Expression (2) and the measured signal intensity S is the minimum, it is possible to quantitatively calculate the transverse relaxation time T2.

The proton density PD can be estimated as a relative value by Expression (3) by measuring sensitivity c of the reception coil with respect to a signal at the position of each pixel using the coefficient K2 of Expression (2).

$$PD = K2/c \quad (3)$$

The longitudinal relaxation rate (R1) and the transverse relaxation rate (R2), which are reciprocals of the longitudinal relaxation time T1 and the transverse relaxation time T2, are also used as physical properties for quantitative diagnosis.

The diffusion coefficient D can be calculated with Expression (4) which is a luminance function in a pulse sequence of a diffusion weighted image.

$$S = S_0 \cdot \text{Exp}[-b \cdot D] \quad (4)$$

In Expression (4), D denotes an apparent diffusion coefficient, b denotes an imaging parameter for adjusting the diffusion weighted degree, and $S_0$ denotes a signal intensity in a case in which a diffusion gradient magnetic field is not applied.

Additionally, various schemes of measuring physical properties in a living body, such as a method of measuring a flow rate in accordance with a phase contrast method, a method of calculating a magnetization ratio in a quantitative susceptibility mapping, and a method of calculating a chemical shift in magnetic resonance (MR) spectroscopy, have been proposed.

In addition to an MRI apparatus, for example, physical properties such as an X-ray absorption coefficient in CT apparatus and reflectivity or an elastic modulus in an ultrasonic diagnosis apparatus can be quantitatively obtained.

A quantitative image in which physical properties of a subject (a biological tissue) calculated in accordance with the foregoing method are used as pixel values can be generated. For example, there are many reports indicating a diagnostic advantage in which a quantitative image is useful for early diagnosis of gonarthrosis or the like. It is easy to standardize MR images difficult to form due to a difference in parameters of apparatuses caused due to hardware when clinical researches are carried out among multiple facilities.

For example, as a diagnosis method of using quantitative images, a method of displaying a plot graphic in which two kinds of selected quantitative values are set as two axes has been proposed (PTL 1). A method of identifying regions of various biological tissues from quantitative values and obtaining a volume has been proposed (PTL 2). A method of calculating a diagnosis image at the time of changing imaging parameters from a relational expression between a quantitative value and luminance of a specific sequence has been proposed (PTL 3).

CITATION LIST

PTL 1: U.S. Pat. No. 8,289,329
PTL 2: U.S. Pat. No. 8,873,822
PTL 3: U.S. Pat. No. 8,874,189

SUMMARY OF INVENTION

Technical Problem

There are many quantitative values which can be measured by an MRI apparatus, as described above. Therefore, in order to determine an abnormal part on the basis of quantitative values in accordance with, for example, the method disclosed in PTL 1, it is necessary for an operator or a diagnostician to compare several graphs or images. Thus, a diagnosis work becomes complex. In the method disclosed in PTL 2, a region of a biological tissue can be identified, but quantitative values may not be directly used for diagnosis. In the method disclosed in PTL 3, obtainable image contrast is limited to an existing sequence and only a weighted image corresponding to each quantitative value can be generated. Accordingly, it is difficult to make diagnosis using several quantitative values efficiently.

The invention is devised in view of the foregoing circumstances and an object of the invention is to provide a supporting technology for enabling diagnosis using a plurality of quantitative values acquired from a medical image acquisition apparatus while reducing a burden on an operator or a diagnostician.

Solution to Problem

According to an aspect of the invention, a medical image diagnosis supporting apparatus includes: a quantitative value reception unit that receives data of two or more predetermined kinds of quantitative values obtained in advance at a plurality of points in a predetermined region of a subject; a variable conversion unit that calculates one or more kinds of intermediate information values which are dependent on the two or more kinds of quantitative values at each of the points using the two or more kinds of quantitative values at each of the points and one or more kinds of predetermined variable conversion functions; and a diagnosis image calculation unit that calculates a diagnosis image for the region. The diagnosis image calculation unit sets a pixel value at each of the points in accordance with a combination of two or more kinds of intermediate information values obtained at each of the points by the variable conversion unit or a combination of one or more of intermediate information values and one or more kinds of quantitative values at the point and generates the diagnosis image.

Advantageous Effects of Invention

According to the invention, it is possible to enable diagnosis using a plurality of quantitative values acquired from a medical image acquisition apparatus while reducing a burden on an operator or a diagnostician. Accordingly, it is possible to reduce the burden on the operator or the diagnostician in quantitative diagnosis in which the quantitative values are used.

BRIEF DESCRIPTION OF DRAWINGS

FIG. 1 is a block diagram illustrating a use image diagnosis supporting apparatus according to a first embodiment.

FIG. 2(a) is an explanatory diagram illustrating a region 10 of a subject and quantitative value of each point, FIG. 2(b) is an explanatory diagram illustrating an intermediate information value of each point, and FIG. 2(c) is an explanatory diagram illustrating a pixel value set at each point and a diagnosis image.

FIG. 3 is a graph illustrating an example of a pixel value setting function according to the first embodiment.

FIG. 4 is an explanatory diagram illustrating an example of a screen for a user interface according to first and second embodiments.

FIG. 5 is a block diagram illustrating a configuration of an MRI apparatus according to the second embodiment.

FIG. 6 is a functional block diagram illustrating a medical image diagnosis supporting unit according to the second embodiment.

FIG. 7 is a flowchart illustrating an operation of the medical image diagnosis supporting unit according to the second embodiment.

FIG. 8 is an explanatory diagram illustrating an example of a screen for a user interface according to a modification example of the second embodiment.

FIG. 9 is an explanatory diagram illustrating an example of a screen for a user interface according to a modification example of the second embodiment.

FIG. 10 is a functional block diagram illustrating a medical image diagnosis supporting unit according to a third embodiment.

FIG. 11 is a flowchart illustrating an operation of a diagnosis image diagnosis supporting unit according to the third embodiment.

FIG. 12 is an explanatory diagram illustrating an example of a screen for a user interface according to the third embodiment.

FIG. 13 is a functional block diagram illustrating a medical image diagnosis supporting unit according to a fourth embodiment.

FIG. 14 is a flowchart illustrating an operation of a diagnosis image diagnosis support unit according to the fourth embodiment.

FIG. 15 is an explanatory diagram illustrating an example of a screen for a user interface according to the fourth embodiment.

DESCRIPTION OF EMBODIMENTS

Embodiments of the invention will be described with reference to the drawings. Throughout all the drawings for describing the embodiments of the invention, the same reference numerals are given to the same functions unless otherwise mentioned and the repeated description thereof will be omitted.

First Embodiment

As in FIG. 1, a medical image diagnosis supporting apparatus 2 according to the embodiment includes a quantitative value reception unit 210, a variable conversion unit 220, and a diagnosis image calculation unit 233 and generates a diagnosis image (see FIG. 2(c)) for supporting diagnosis of a doctor or the like in regard to a predetermined region 10 of a subject.

As illustrated in FIG. 2 (a), the quantitative value reception unit 210 receives data of two or more predetermined kinds of quantitative values obtained in advance in a plurality of points 20-1 to 20-n in the predetermined region 10 of the subject. Any kind of quantitative value may be used as long as the kinds of quantitative values indicate characteristics of the subject. For example, a physical property of a tissue of the subject, a pixel value of a subject image imaged so that a specific physical property is weighted, a characteristic value in the subject obtained by an agent such as a contrast agent administered to the subject, or a physical amount or a physical property obtained by radiating and measuring acoustic or electromagnetic waves to the subject can be used as the quantitative value. Examples of the physical property of a tissue of the subject obtained using a nuclear magnetic resonance phenomenon include a longitudinal relaxation time T1, a longitudinal relaxation rate, a transverse relaxation time T2, a transverse relaxation rate, a chemical shift of a precession frequency in nuclear spin of the subject, a proton density PD in the subject, magnetic susceptibility, a diffusion coefficient of a molecule in the subject, and a flow rate of a liquid such as blood. Additionally, example of physical amount indicating characteristics of the subject includes an RF radiation intensity. Examples of physical properties measured by radiating acoustic waves to the subject include an acoustic velocity, an elastic modulus, stress, and an attenuation amount. A physical property measured by radiating the X ray includes an X-ray absorption coefficient. In the example of FIG. 2(a), the quantitative value reception unit 210 receive three kinds of quantitative values x, y, and z at points 20-1 to 20-n in the region 10.

The variable conversion unit 220 calculates one or more kinds of intermediate information values which are dependent on the two or more kinds of quantitative values x, y, and z at each point using two or more kinds of quantitative values at the points 20-1 to 20-n received by the quantitative value reception unit 210 and one or more predetermined variable conversion functions. For example, as in FIG. 2(b), two kinds of intermediate information values F1 and F2 which are dependent on the quantitative values x, y, and z are calculated at each point using quantitative values $(x_1, y_1,$ and $z_1)$ of the point 20-1, quantitative values $(x_2, y_2,$ and $z_2)$ of the point 20-2, the quantitative values $(x_n, y_n,$ and $z_n)$ of the point 20-n, and the predetermined variable conversion functions. In the example of FIG. 2(b), the calculated intermediate information values $(F1_1$ and $F2_1)$ of the point 20-1, the intermediate information values $(F1_2$ and $F2_2)$ of the point 20-2, and the quantitative values $(F1_n$ and $F2_n)$ of the point 20-n are calculated.

The diagnosis image calculation unit 233 sets a pixel value at each point in accordance with a combination of the intermediate information values F1 and F2 of each point obtained by the variable conversion unit 220 or a combination of the intermediate information value F1 (or F2) and one or more kind of quantitative values (one or more of x, y, and z). A diagnosis image is generated by disposing the set pixel values of each point at the position of each point. For example, the diagnosis image calculation unit 233 obtains the pixel values corresponding to a combination of the intermediate information values F1 and F2 of each point with reference to a pixel value setting function, a table, or the like indicating a relation between the pixel values of the combination of the intermediate information values F1 and F2 determined in advance. For example, as indicated with the form of the graph of FIG. 3, the diagnosis image calculation unit 233 obtains the pixel values corresponding to the combination of the intermediate information values $F1_1$ and $F2_1$ of the point 20-1 with reference to a function or a table in which one pixel value is allocated to the combination of the intermediate information values F1 and F2, as indicated with the form of the graph in FIG. 3. Similarly, a pixel value corresponding to the combination f the intermediate information values $F1_2$ and $F2_2$ of the point 20-2 and a pixel value corresponding to the combination of the quantitative values $F1_n$ and $F2_n$ of the point 20-n are obtained. The diagnosis image calculation unit 233 calculates a diagnosis image in the region 10 by disposing the obtained pixel values at the positions 20-1, 20-2, and 20-n.

The diagnosis image calculation unit 233 sets a pixel value with reference to a function or a table determined in advance according to, for example, the combination of the intermediate information value F1 and the quantitative value x in a case in which the pixel value is set according to the combination of the intermediate information value F1 (or F2) and one or more kinds of quantitative values (one or more of x, y, and z).

The combination of two or more kinds of intermediate information values or the combination of one or more kinds of intermediate information values and one or more kinds of quantitative values are not limited to the combination of two values. A combination of three or more kinds of intermediate information values, a combination of two or more kinds of intermediate information values and one or more kinds of quantitative values, or a combination of one or more kinds of intermediate information values and two or more kinds of quantitative values can also be used.

As described above, the medical image diagnosis supporting apparatus according to the embodiment can generate one diagnosis image which is dependent on two or more kinds of quantitative values from the quantitative values. Therefore, it is not necessary for an operator or a diagnostician to compare a plurality of quantitative values or a plurality of quantitative images, and it is possible to support diagnosis using the plurality of quantitative values while reducing a burden on the operator or the diagnostician.

The variable conversion unit 220 preferably calculates intermediate information values which have less number of kinds than that of quantitative values received by the quantitative value reception unit 210. Thus, since dimension reduction can be performed through variable conversion, the diagnosis image calculation unit 233 can easily calculate a diagnosis image.

The diagnosis image calculation unit 233 may include a display control unit that generates an image indicating a distribution of two or more kinds of intermediate information values (F1, F2, and the like) of each point or a distribution of combinations of the values, or a distribution of one or more kinds of intermediate information values (F1 and F2) and one or more kinds of quantitative values (x, y, and z), or a distribution of combinations of the values used to generate the diagnosis image and causes a connected display device to display the image. For example, as in FIG. 4, the display control unit displays the diagnosis image in a region 403 of a display screen 400 of a display device and displays the distribution of the combinations of the intermediate information values as an image such as histogram in a region 402.

When a pixel value is set at each point, the diagnosis image calculation unit 233 preferably set the pixel value so that the fact that the combination of values of the two or more kinds of intermediate information values (F1, F2, and the like) or the combination of one or more kinds of intermediate information values (F1, F2, and the like) and one or more kinds of quantitative values (x, y, z, and the like) is a predetermined value is weighted in the diagnosis image. For example, as in FIG. 3, a pixel value is set using a function or a table determined so that a combination ($F1_a$ and $F2_a$) of a predetermined intermediate information value F1 and a predetermined intermediate information value F2 takes a maximum value of the pixel values. Thus, when the combination of the predetermined values (the combination of the intermediate information values F1a and F1a) is taken, a weighted image can be generated as the diagnosis image. Therefore, it is possible to further support diagnosis of the operator or the diagnostician.

The variable conversion unit 220 may use a function determined in advance as a variable conversion function used to calculate the intermediate information values F1 and F2 or the like, or include a function calculation unit that obtains the variable conversion function by calculation using the quantitative values x, y, and z at the plurality of points 20-1, 20-2, and 20-$n$ received by the quantitative value reception unit. In this case, the function calculation unit preferably sets the variable conversion function so that a variance of the intermediate information values at the plurality of points 20-1, 20-2, and 20-$n$ increases. By increasing the variance of the intermediate information values after the variable conversion, it is possible to easily separate a plurality of peaks indicated by the combination of the intermediate information values F1 and F2 or the like, and thus weight and display characteristics of the subject indicated by the plurality of kinds of quantitative values with other pixel values. For example, the function calculation unit can obtain the variable conversion function in which the variance of the intermediate information values increases by generating a variance-covariance matrix of the quantitative values x, y, and z at the plurality of points, obtaining principal components of the variance-covariance matrix and setting the principal components as coefficients, and obtaining a linear polynomial in which two or more quantitative values are variables as the variable conversion function. The invention is not limited to analysis of the principal components. The variable conversion function can also be obtained by performing a process including one of a process of converting a function with any form, a scaling process, a segmentation process, and a singular value decomposition process.

Second Embodiment

A more detailed embodiment of the medical image diagnosis supporting apparatus will be described as a second embodiment. In the second embodiment, a magnetic resonance imaging (MRI) apparatus including a medical image diagnosis supporting apparatus will be described. The medical image diagnosis supporting apparatus generates a diagnosis image using two or more kinds of quantitative values acquired by the MRI apparatus.

First, the magnetic resonance imaging (MRI) apparatus including the medical image diagnosis supporting apparatus according to the embodiment will be described.

The MRI apparatus is a medical image diagnosis apparatus that mainly uses a proton NMR phenomenon. The MRI apparatus can image any cross section of a subject in a noninvasive manner and can acquire information regarding a biological function such as a blood flow or metabolism in addition to morphological information.

FIG. 5 is a block diagram illustrating a typical configuration of an MRI apparatus 100 according to the embodiment. The MRI apparatus 100 according to the embodiment includes a magnet 101 that generates a static magnetic field, a gradient magnetic field coil 102 that generates a gradient magnetic field, an RF coil 107 that radiates a high-frequency magnetic field pulse to a subject (a living body) 103, an RF probe 108 that detects an echo signal generated from the subject 103, and a bed (table) 115 on which the subject (for example, a living body) 103 is placed inside a space of the generated static magnetic field of the magnet 101.

The MRI apparatus 100 further includes a gradient magnetic field power supply 105 that drives the gradient magnetic field coil 102, a high-frequency magnetic field generator 106 that drives the RF coil 107, a receiver 109 that detects an echo signal detected with the RF probe 108, and a sequencer 104. The sequencer 104 sends a command to the gradient magnetic field power supply 105 and the high-frequency magnetic field generator 106, generates a gradient magnetic field and a high-frequency magnetic field, respectively, and sets a nuclear magnetic resonance frequency serving as a detection reference in the receiver 109. In addition to the units, the MRI apparatus 100 includes a computer 110 that performs signal processing on a signal detected by the receiver 109, a display device 111 that displays a processing result in the computer 110, a storage device 112 that retains the processing result, and an input device 116 that receives an instruction from a user. The storage device 112 retains various kinds of data necessary for a process in the computer 110.

In a case in which it is necessary to adjust uniformity of the static magnetic field, the MRI apparatus 100 may further include a shim coil 113 and a shim power supply 114 that drives the shim coil 113. The shim coil 113 includes a plurality of channels and generates an additional magnetic field to correct non-uniformity of the static magnetic field by a current supplied from the shim power supply 114. The current allowing to each channel included in the shim coil 113 at the time of adjustment of the uniformity of the static magnetic field is controlled by the sequencer 104.

In a case in which imaging is performed on a desired imaging region (imaging cross section) of a subject by the MRI apparatus 100 with the foregoing configuration, the computer 110 outputs an instruction to the sequencer 104 so that each unit operates at a timing and with the degree in accordance with a preset program and controls the operation of each unit included in the MRI apparatus 100. When the sequencer 104 sends commands to the gradient magnetic field power supply 105 and the high-frequency magnetic field generator 106, an RF pulse is applied to the subject 103 via the RF coil 107 at a timing instructed from the computer 110 and a gradient magnetic field pulse, such as a slice selection or phase encoding gradient magnetic field or a read-out gradient magnetic field, for giving positional information to an echo signal is applied by the gradient magnetic field coil 102. An NMR signal (echo signal) for generating nuclear magnetization is received by the RF probe 108 and is detected (measured) by the receiver 109. The NMR signal is measured repeatedly until a measurement space called the k space is charged. The measured signal is sent to the computer 110. The computer 110 reconstructs an image by performing inverse Fourier transform on the signal charged in the k space. The storage device 112 stores the generated image and stores the detected signal, imaging conditions, and the like as necessary.

In addition, of the programs executed by the computer 110, a program particularly describing timings or intensities of the high-frequency magnetic field and the gradient magnetic field and a reception timing of a signal is called a pulse sequence. Imaging is performed in accordance with the pulse sequence and imaging parameters necessary to control the pulse sequence. By controlling the timings and the intensities of the high-frequency magnetic field and the gradient magnetic field set by the pulse sequence, it is possible to image any imaging cross section of a subject. The pulse sequence is generated in advance and retained in the storage device 112 and the imaging parameters are input via the input device 116 by the user. The computer 110 controls user interfaces of the input device 116, the display device 111, and the like, receives inputs, and causes the display device 111 to display the generated images.

Various pulse sequences are known according to purposes. For example, a gradient echo (GrE) type of high-speed imaging method is a method of sequentially changing a phase encoding gradient magnetic field at each repetition time (hereinafter referred to as a TR) of the pulse sequence and measuring the number of NMR signals necessary to obtain one tomographic image. The imaging parameters include the repetition time TR, the echo time TE, a flip angle α determining the intensity of an RF pulse, and a coordinate phase θ and can be set according to an image desired to be imaged.

By setting an imaging part desired to be diagnosed in the subject using an image acquired through imaging for positioning and setting a pulse sequence or a imagine parameter in accordance with a physical property desired to be weighted and imaged, it is possible to capture images in which a plurality of kinds of physical properties are weighted (for example, a T1 weighted image, a T2 weighted image, FLAIR, a diffusion weighted image, an MRA). By repeatedly capturing a weighted image a plurality of times while changing the imaging parameters and processing obtained signals, it is possible to calculate a plurality of physical properties such as T1, T2, a proton density (PD), magnetic susceptibility, and a diffusion coefficient of a subject tissue at the position of each pixel of an image. Thus, it is also possible to generate a T2 image, a PD image, and a T1 image in which T1 is set as a pixel value.

The computer 110 according to the embodiment includes a medical image diagnosis unit 200 that generates a diagnosis image using two or more kinds of quantitative values of each pixel, such as a pixel value (physical property) of a T1 image, a T2 image, a PD image, or the like, a pixel value of a weighted image such as a T1 weighted image or a T2 weighted image, and a quantitative value measurable in the MRI apparatus 100, and a value input from a user, as inputs. Specifically, the computer 110 includes a CPU and a memory and is configured to realize a function of each unit of the medical image diagnosis unit 200 by software by allowing the CPU to read a medical image diagnosis program stored in advance in the memory and execute the medical image diagnosis program. Here, the medical image diagnosis unit 200 according to the embodiment is not limited to the realization of the functions by software. Some or all of the functions can also be realized by hardware such as a custom IC such as ASIC or a programmable IC such as FPGA.

As illustrated in FIG. 6, the medical image diagnosis supporting unit 200 according to the embodiment includes a quantitative value reception unit 210, a variable conversion unit 220, a diagnosis image generation unit 230, and a diagnosis image display unit 240. The quantitative value reception unit 210 according to the embodiment receives two or more kinds of quantitative values at each pixel (point) of an image calculated by the MRI apparatus in a desired region (cross section) of a subject. The variable conversion unit 220 includes a function calculation unit 221 that obtains a function used for variable conversion by calculation based on the quantitative values received by the quantitative value reception unit 210. The variable conversion unit 220 calculates one or more kinds of intermediate information values at each pixel using the variable conversion function obtained by the function calculation unit 221 and the quantitative values received by the quantitative value reception unit 210 as in the first embodiment. The diagnosis image generation unit 230 includes an image generation input variable selection unit 231, an image generation input variable display unit 232, and a diagnosis image calculation unit 233. The image generation input variable selection unit 231 selects two or more kinds of values (input variables) used to generate an image from one or more kinds of intermediate information values calculated by the variable conversion unit 220 and the quantitative values (hereinafter referred to as input variables fitted to the intermediate information values and the quantitative values) received by the quantitative value reception unit 210. The two kinds of values are selected so that the two or more input variables include at least one kind of intermediate information value. The image generation input variable display unit 232 generates an image indicating a distribution of two or more kinds of input variables selected by the image generation input variable selection unit 231 or a distribution of combination of the values and performs display control such that the display device 111 performs display. The diagnosis image calculation unit 233 sets a pixel value for each pixel in accordance with a combination of the values of the input variables and generates a diagnosis image as in the first embodiment.

Hereinafter, an operation of the medical image diagnosis supporting unit 200 according to the embodiment will be described with reference to the flow of FIG. 7. First, an overview of the operation will be described.

When the user gives an instruction via user interfaces (the display device 111 and the input device 116), the quantitative value reception unit 210 receives (reads) data of a plurality of kinds of quantitative values (x, y, z, . . . ) for each pixel from the storage device 112 of the MRI apparatus (step S301). Subsequently, the function calculation unit 221 of the variable conversion unit 220 calculates variable conversion functions f1(x, y, z, . . . ), f2(x, y, z, . . . ), f3(x, y, z, . . . ), and the like by calculation using the data of the plurality of kinds of quantitative values (x, y, z, . . . ) received in step S301 (step S302-1). The variable conversion unit 220 calculates intermediate information values F1(=f1(x, y, z, . . . )), F2(=f2(x, y, z, . . . )), F3(=f3(x, y, z, . . . )), and the like which are dependent on the two or more kinds of quantitative values (x, y, z, . . . ) received in step S301 for each pixel using the calculated variable conversion functions (step S302-2). Subsequently, the image generation input variable selection unit 231 selects two or more image generation input variable (the quantitative values and/or the intermediate information values) so that at least one intermediate information value (for example, F1) is included setting the data of the quantitative values (x, y, z, . . . ) for each pixel received in step S301, the intermediate information values F1, F2, and F3 for each pixel calculated in step S302, and the like as candidates for an image generation input variable (step S303). Subsequently, input variable display unit 232 generates an image displaying a distribution of the input variables (the two or more intermediate information values (for example, F1 and F2) or a combination (for example, F1 and x) of the intermediate information value and the quantitative position (for example, F1 and x)) selected in step S303 and displays the image in the display device 111 (step S304). Subsequently, the diagnosis image calculation unit 233 allocates a pixel value to the pixel in accordance with a combination of values of the image generation input variables (for example, F1 and F2) selected in step S303, generates a diagnosis image, and causes the display device 111 to display the diagnosis image (steps S305 and S306).

The operation of steps S301 to S306 will be described in more detail. In step S301, the medical image diagnosis support unit 200 first displays the screen 400 for a user interface illustrated in FIG. 4 on the display device 111. The screen 400 includes a quantitative value reading instruction reception region 401 displayed in a button shape for instructing to start reading a quantitative value, an input variable display region 402 in which input variables (a combination of two or more intermediate information values or a combination of the intermediate information value and the quantitative value) used to generate an image are displayed in a predetermined format, and a diagnosis image display region 403 in which a diagnosis image is displayed. When the user operates (clicks) the button of the instruction reception region 401 using the input device 116 including a mouse or a keyboard, the quantitative value reception unit 210 reads the two or more kinds of quantitative values retained in the storage device 112 (step S301). The two or more kinds of quantitative values retained in the storage device 112 are pixel values of two or more images among an image, a T1 weighted image, a T2 weighted image, and the like with the physical properties (T1, T2, proton density (PD), magnetic susceptibility, a diffusion coefficient, and the like) in the predetermined region 10 of the subject calculated from NMR signals measured by executing the pulse sequence by the MRI apparatus. The kinds of received quantitative values may be the kinds of values determined in advance or may be the kinds of values set by the user at the time of MRI measurement, or a selection of the kinds of quantitative values may be received via the user interface from the user in step S301. Hereinafter, a case in which three kinds of data, T1, T2, and PD are received for each pixel as quantitative data will be described as an example. A data format may be any format such as 1-dimensional vector data, 2-dimensional array data, or 3-dimensional array data.

In step S302-1, the function calculation unit 221 of the variable conversion unit 220 calculates the variable conversion functions f1 and f2 by calculation using the quantitative value data T1, T2, and PD received by the quantitative value reception unit 210. Hereinafter, a case in which three kinds of values T1, T2, and PD, are used as quantitative values x, y, and z to be input to the variable conversion unit and two kinds of functions, the variable conversion functions f1 and f2, are calculated will be described. The storage device 112 stores functions expressed with Expressions (5) and (6) below as basic functions of calculating the variable conversion functions f1 and f2 in the storage device 112.

$$f1(T1,T2,PD)=A1 \cdot T1+B1 \cdot T2+C1 \cdot PD+D1 \tag{5}$$

$$f2(T1,T2,PD)=A2 \cdot T1+B2 \cdot T2+C1 \cdot PD+D2 \tag{6}$$

In Expressions (5) and (6), A1, A2, B1, B2, C1, C2, D1, and D2 are coefficients. The function calculation unit 221 calculates a value of each coefficient based on the quantitative data of each pixel received in step S301. Here, a method of determining the value of each coefficient by principal component analysis using the data of the quantitative values T1, T2, and PD of all the pixels will be described as an example. The coefficients of the variable conversion functions f1 and f2 can be set using the principal component analysis so that variances of the intermediate information values F1 and F2 calculated using the variable conversion functions f1 and f2 increase. Since the variances of the intermediate information values F1 and F2 increase, a plurality of peaks indicated by the combinations of the intermediate information values F1 and F2 and the like are easily separated, and thus characteristics of the subject indicated by the plurality of kinds of quantitative values can be weighted with different pixel values to be displayed.

First, an average of all the pixels is obtained at each of the quantitative values T1, T2, and PD by Expression (7). A variance-covariance matrix S of all the pixels of each quantitative value is obtained by the obtained average and Expression (8). Here, in Expressions (7) and (8), N is the number of pixels.

$$\overline{X}_i = \frac{1}{N}\sum_{n=1}^{N} X_i, \quad X_1 = T1, \ X_2 = T2, \ X_3 = PD \tag{7}$$

$$S = \begin{pmatrix} S_{11} & S_{12} & S_{13} \\ S_{21} & S_{22} & S_{23} \\ S_{31} & S_{32} & S_{33} \end{pmatrix}, \quad S_{i,j} = \frac{1}{N}\sum_{n=1}^{N}(X_i - \overline{X}_i)(X_j - \overline{X}_j) \tag{8}$$

Subsequently, pairs of eigenvectors x and eigenvalues λ of the variance-covariance matrix S satisfying Expression (9) below are obtained. Here, the eigenvalue X is a number which is not zero.

$$S\vec{x}=\lambda\vec{x} \tag{9}$$

Here, the eigenvector x is a vector that has a length of 1 3-dimensionally. In a case in which the variance-covariance matrix S is a real symmetric matrix as in the embodiment, the eigenvalue λ is known to be a real number. The pairs of eigenvectors x and eigenvalues λ can be obtained using the Jacobi method or the like. The eigenvectors x can be obtained in three ways so that the eigenvectors x are perpendicular to each other. Of the obtained three eigenvectors x, two eigenvectors x are selected from larger eigenvalues λ and are set as eigenvectors x1 and x2. Three components of the eigenvectors x1 and x2 are determined as coefficients A1, A2, E1, B2, C1, and C2 as in Expression (10).

$$\begin{pmatrix} A1 \\ B1 \\ C1 \end{pmatrix} = \overline{x1}, \begin{pmatrix} A2 \\ B2 \\ C2 \end{pmatrix} = \overline{x2} \quad (10)$$

On the other hand, D1 and D2 are calculated with Expression (11) below.

$$D1 = -(\overline{X}_1, \overline{X}_2, \overline{X}_3)\begin{pmatrix} A1 \\ B1 \\ C1 \end{pmatrix}, D2 = -(\overline{X}_1, \overline{X}_2, \overline{X}_3)\begin{pmatrix} A2 \\ B2 \\ C2 \end{pmatrix} \quad (11)$$

The function calculation unit 221 stores the values of the coefficients calculated by the principal component analysis in the storage device 112, as described above. In step S302-2, the variable conversion unit 220 reads Expressions (5) and (6) stored in advance in the storage unit 112 and applies the values of the coefficients calculated in step S302-1 to obtain the variable conversion functions f1 and f2. Then, the values of the quantitative values T1, T2, and PD received at each pixel in step S301 are read from the storage device 112, the variable conversion functions f1 and f2 are applied, and the intermediate information values F1(=f1(T1, T2, PD)) and F2(=f2(T1, T2, PD)) are obtained for each pixel. Thus, it is possible to obtain the two intermediate information values F1 and F2 which are dependent on the data of the three different quantitative values, T1, T2, and PD.

Expressions (5) and (6) express multivariable linear functions for variable conversion of the three kinds of quantitative values T1, T2, and PD, but the number of kinds of quantitative values is not limited to three kinds of quantitative values, but two or more kinds of quantitative values may be used. In step S302-2, the intermediate information values F1 and F2 are obtained for each pixel. The coefficients of Expressions (5) and (6) are common between the pixels, and thus the same values are used. In the embodiment, the example in which the function calculation unit 221 calculates the coefficients in step S302-1 has been described. However, values of coefficients determined in advance and stored in the storage device 112 may be read and used in step S302-2.

In step S303, the image generation input variable selection unit 231 selects two or more variables from the intermediate information values F1 and F2 calculated in step S302-2 and the quantitative values T1, T2, and PD received in step S301. A selection of the combinations of the selected variables by the user may be combinations stored in advance in the storage device 112 or the variables may be received through the user interface. For example, in a case in which the intermediate information values F1 and F2 are stored to be selectable in the storage device 112, the image generation input variable selection unit 231 selects the intermediate information values F1 and F2 as image generation input variables with reference to them.

The image generation input variable display unit 232 generates a display image so that it can be understood how the variables (the intermediate information values F1 and F2) of the pixels or the combinations of the F1 and F2 are distributed in a variable space.

For example, a graph (the region 402 in FIG. 4) in which the image generation input variables (the intermediate information values F1 and F2) are set as axis directions is generated. The graph represents a distribution (simultaneous or isomerous distribution) of a frequency $N_{pq}$ in a case in which the combinations of the intermediate information values F1 and F2 of the pixels are plotted on coordinates divided into Q sections at the equal interval P between the minimum value and the maximum value of the intermediate information values F1 and F2. The graph is obtained with Expression (12).

$$N_{pq} = \sum_i 1, (0 < i < i_{max}, F1_p < F1_i \le F1_{p+1}, F2_q < F2_i \le F2_{q+1}) \quad (12)$$

In Expression (12), imax is the number of all pixels, F1p is a minimum value of a p-th section, F2q is a minimum value of a q-th section of F2. F1i is values of F1 and F2 of an i-th pixel when numbers are uniquely allocated to all the pixels from 1 in all the pixels. The frequency Npq is calculated in each of p from 1 to P and q from 1 to Q. In the calculated frequency distribution, a value of Npq can be displayed in the form of a 3-dimensional histogram in which two axes of a 2-dimensional plane are set to F1 and F2 and an axis (height) perpendicular to the two axes corresponds to the frequency Npq, as in the graph of the region 402 in FIG. 4. On the two axes of the simultaneous distribution, letters such as first and second principal components may be displayed as names of the intermediate information values F1 and F2, respectively.

In step S305, the diagnosis image calculation unit 233 generates a diagnosis image by allocating the pixel values in accordance with the combinations of the values of the image generation input values (the intermediate information values F1 and F2) for each pixel. In the generation of the diagnosis image, for example, a pixel value setting function and calculation parameters stored in advance in the storage device 112 are used. Here, a case in which the diagnosis image is calculated using a Gauss function as the pixel value setting function will be described.

The storage device 112 stores Expression (13) below as a pixel value setting function G which is dependent on F1 and F2 in advance.

$$G(F1,F2) = \text{Exp}[-\{(F1-U)^2 + (F2-V)^2\}/(W^2)] \quad (13)$$

In Expression (13), U, V, and W are constants. Values stored in advance as calculation parameters in the storage device 112 may be used as values of U, V, and W or values received through the user interface from the user may be used. In Expression (13), a largest pixel value G of a pixel in which the intermediate information value E1 is a value U and the intermediate information value F2 is a value V, that is, a pixel of (F1, F2)=(U, V), is taken, and a smaller pixel value is received as the intermediate information values F1 and F2 are farther from U and V, respectively. W is a coefficient that determines a weighted degree of a pixel value which is set as a large pixel value by determining how far the intermediate information values F1 and F2 are separated from U and V. That is, Expression (13) is a function of weighting similarity of the image calculation input variable with a specific combination. The diagnosis image calculation unit 233 can obtain the pixel value G by substituting the F1 and F2 of the pixel to Expression (13) for each pixel (step S305). Thus, as the combinations of the intermediate information values F1 and F2 are closer to F1=U and F2=V in the pixel, a diagnosis image weighted with the large pixel value is generated.

The values of the constants U, V, and W in Expression (13) can also be obtained by calculation in accordance with a biological tissue (hereinafter referred to as a target tissue) desired to be weighted. Various biological tissues have combinations of quantitative values (for example, T1=1.3 seconds and T2=0.1 seconds in gray matter) inherent in each kind of biological tissue. Accordingly, standard quantitative values of a target tissue are obtained from quantitative data or the like of a healthy person and are stored in the storage device 112. The diagnosis image calculation unit 233 reads the image generation input variables (for example, the intermediate information values F1 and F2) selected in step S303 and obtain values of the image generation input variables (for example, the intermediate information values F1 and F2) of the target tissue by calculation. Specifically, the values of the standard T1, T2, and PD of the target tissue and the values of the coefficients in Expressions (5) and (6) are read from the storage device 112 and are substituted to Expressions (5) and (6) corresponding to the image generation input variables (for example, the intermediate information values F1 and F2) selected in step S303. Thus, the standard intermediate information values F1 and F2 of the target tissue are calculated. The calculated standard F1 of the target tissue is assumed to be U and the standard F2 is assumed to be V.

Since W is a constant for changing the weighted degree, any value (for example, W=1) may be set, or a value obtained by calculation so that approximate ranges of the F1 and F2 taken by the target tissue are weighted may be set. In a case in which W is obtained by calculation, standard deviations of the standard T1, T2, and PD of the target tissue are obtained in advance and a standard deviation of the intermediate information value F1 is calculated and set as W using a formula of the standard deviation of the sum.

The constants U, V, and W for weighting each target tissue can be obtained in advance for each target tissue by the foregoing calculation and the results can also be stored in the storage device 112. Thus, a selection of a tissue desired to be weighted from the user can be received via the user interface or the like by the diagnosis image calculation unit 233 and the constants U, V, and W corresponding to the selected tissue can be read from the storage device 112 to be used. Thus, it is possible to calculate a diagnosis image in which the target tissue is weighted.

The diagnosis image calculation unit 233 displays the generated diagnosis image in a predetermined format on the display device 111. For example, the pixel values of the diagnosis image are caused to correspond to the luminance and the diagnosis image is displayed as a grayscale image in the diagnosis image display region 403 of the display device 111 as in FIG. 4. Alternatively, in a case in which the diagnosis image is 3-dimensional, the diagnosis image can be converted into a planar image by a ray tracing method or the like or a luminance value on a predetermined cross section can also be displayed as a grayscale image. Alternatively, a method of displaying the diagnosis image on the display device 111 through image display software different from the medical image diagnosis supporting apparatus according to the embodiment may be used.

As described above, in the embodiment, one diagnosis image with the pixel values in accordance with the combination of the values such as the intermediate information values can be generated and display by performing the conversion into two or more input variables (the combination of two or more intermediate information values or the combination of the intermediate information value and the quantitative value) based on the plurality of kinds of quantitative values. Further, two or more kinds of input variables (the combination of the intermediate information values or the combination of the intermediate information value and the quantitative value) can be displayed in the form of the simultaneous distribution or the like for the user. Each tissue of a living body has a combination of quantitative values inherent to each kind of tissue. Therefore, by using the diagnosis image according to the embodiment, it is possible to identify a kind of tissue or an abnormal tissue from one diagnosis image without performing a complicated work of comparing a plurality of pieces of quantitative data to each other. By displaying an image indicating input variables (the combination of the intermediate information values or the combination of the intermediate information value and the quantitative value) along with the diagnosis image, it is possible to efficiently visualize a difference in a combination of the quantitative values which may not be confirmed with individual quantitative values to use the difference in the combination of the quantitative values for diagnosis.

In the embodiment, the variable conversion function is calculated using the principal component analysis so that the variance of the intermediate information values at the plurality of pixels increases. Therefore, it is possible to obtain the intermediate information values in which a difference in the combination of the quantitative values is reflected. Accordingly, even when there is a difference which may not be confirmed due to overlapping of frequency peaks in regard to the individual quantitative values, the frequency peaks can be efficiently separated and displayed with other pixel values by using the intermediate information values obtained by performing the variable conversion on the quantitative values.

In the above-described embodiment, the method in which the principal component analysis is used to obtain the variable conversion function of increasing the variance of the intermediate information values has been described. However, the coefficients of the variable conversion function may be stored in advance in the storage device. For example, a healthy subject or a subject with a disease may be measured in advance, coefficients may be obtained through principal component analysis, and the coefficients may be used as coefficients at the time of subsequent examination. Thus, numerical values of the intermediate information can be compared between subjects, and thus an improvement in diagnosability can be expected.

In the foregoing embodiment, the example in which the MRI apparatus is used as a medical image acquisition apparatus and the medical image diagnosis supporting apparatus 200 is mounted on the MRI apparatus has been described. However, the medical image acquisition apparatus is not limited to the MRI apparatus. For example, the medical image diagnosis supporting apparatus may be mounted on a CT apparatus, an ultrasonic diagnosis apparatus, or the like. In a CT apparatus, X-ray absorption coefficients may be measured and used as quantitative values. In an ultrasonic diagnosis apparatus, an elastic modulus, an acoustic velocity, or the like may be measured and used as quantitative values.

Modification Example 1 of Second Embodiment

In the second embodiment, the variable conversion unit 220 is configured to output two intermediate information values using two multivariable linear functions as in Expressions (5) and (6). However, the variable conversion function is not limited to the linear function. For example, instead of the intermediate information values F1 or F2 output by the variable conversion unit 220, an intermediate information value F3 (=f3 (T1, T2)) can also be calculated using one function f3 in which an exponential function or the like is combined as expressed in Expression (14).

$$f3(T1,T2)=\{1-\text{Exp}(-A/T1)\}\text{Exp}(-B/T2) \quad (14)$$

In Expression (14), A and B are conversion parameters. For example, when A=1.5 and B=1.5, the intermediate information value F3 takes a larger value in a tissue in which T2 is longer than 1.5 seconds than in a tissue in which T2 is equal to or less than 1.5 seconds. Thus, for example, a brain region, an effect of weighting differences in combinations of T1 and T2 between blood, cerebral spinal fluid, and cerebral parenchyma can be further improved than in a case in which the linear function is used as the conversion function. By allocating pixel values in accordance with the value of the intermediate information value F3 without combining two intermediate information values, it is also possible to generate a diagnosis image in which blood, cerebral spinal fluid, and cerebral parenchyma are indicated by different pixel values, for example, in a brain region.

In addition to Expression (14), a multidimensional polynomial, a logarithmic function, a trigonometric function, a Sigmoid function, and a function in which these functions are combined may be appropriately set in accordance with the kinds of quantitative data received by the quantitative value reception unit and this function may be used as the variable conversion function. Thus, the effect of weighting the difference in the combination of the quantitative values can be further improved than in the case in which the linear function is used as the variable conversion function.

Modification Example 2 of Second Embodiment

In the above-described embodiment, a scale adjustment processing function f4 expressed in Expression (15) may be used as the variable conversion function of the variable conversion unit 220 to calculate an intermediate information value F4 (=f4 (T1)).

$$f4(T1)=\text{Exp}(-A'/T1) \quad (15)$$

In Expression (15), A' is a conversion parameter. In the modification example, the quantitative data used in the variable conversion unit 220 is only T1, while a tissue in which T1 is short is distributed in a range in which the intermediate information value F4 is broad, a tissue in which T1 is long is concentrated in a range in which the intermediate information value F4 is narrow. Thus, different scale adjustment is performed depending on whether the T1 of a tissue is long or short, conversion dependent on two or more different quantitative values is performed. Thus, distributions of pixel values of a tissue in which T1 is long and a tissue in which T1 is short can be converted at an adjusted scale. Accordingly, when a distribution of the intermediate information values or the like is displayed by the image generation input variable display unit 232, there is the advantageous effect in which that a user can easily understand tissues in which T1 is different.

Modification Example 3 of Second Embodiment

In the second embodiment, as described above, the combination of the intermediate information value and the quantitative value may be selected by the image generation input variable selection unit 231. A specific example will be described below. For example, the intermediate information value F3 calculated using the function of Expression (14) and a flow rate v can be selected as an input variable. At this time, the diagnosis image calculation unit 233 can allocate a pixel value to a combination of the intermediate information value F3 and a value of the flow rate v as in Expression (16).

$$G(F3, v) = \begin{cases} 1 & \text{if } v \geq C1, \text{ and, } F3 > C2 \\ 0 & \text{if } v < C1, \text{ or, } F3 < C2 \end{cases} \quad (16)$$

In Expression (16), C1 and C2 are conversion parameters stored in advance in the storage device 112. By using Expression (16), it is possible to further separate a difference between blood and cerebral spinal fluid weighted with the intermediate information value F3 in accordance with a velocity v and allocate an image value. Therefore, it is possible to generate a diagnosis image in which only a blood vessel figure is weighted. In this way, in a case in which the combination of the intermediate information value and the quantitative value is selected as the input variable, a diagnosis image in which the difference in the combination of the quantitative values is weighted can be obtained. In addition, both the quantitative value and the intermediate information value dependent on the plurality of quantitative values are displayed for the user by the diagnosis image calculation unit 232. Accordingly, there is the advantageous effect of enabling diagnosis using the quantitative values while reducing a burden of individually confirming quantitative values.

Modification Example 4 of Second Embodiment

The variable conversion function used in the variable conversion unit 220 according to the second embodiment is not limited to a function capable of obtaining continuous values in regard to the quantitative values. A variable conversion function of outputting discrete values may be used. For example, a function of identifying kinds of biological tissues (hereinafter referred to as types of biological tissues; for example, cerebral spinal fluid, white matter, and gray matter) from input quantitative values and outputting numerical values corresponding to the types of biological tissues can be used as the variable conversion function. In the identifying of the types of biological tissues, a method such as a nearest neighbor algorithm, linear identification, or maximum likelihood estimation can be used. Hereinafter, a variable conversion function in which the nearest squares algorithm is used setting T1, T2, and PD as inputs will be described.

First, quantitative values of a healthy subject are measured and representative quantitative values of the types of biological tissues are stored in the storage device 112. Specifically, for example, in an image (shape image) such as a T1 weighted image in which the shape of a biological tissue can be clearly determined, a representative pixel present in a certain type of biological tissue is selected by a diagnostician and various quantitative values in the selected pixel are obtained. A combination of various quantitative values in the selected pixels is stored as a combination of representative quantitative values of the types of biological tissues in the storage device 112. This process is performed on a plurality of types of biological tissues. Thus, a combination of representative quantitative values in each of the plurality of types of biological tissues is stored in advance in the storage device 112.

The variable conversion unit 220 obtains the combination of the quantitative values in each pixel of an image obtained by imaging an examination target subject using the image and determines which combination of the quantitative values of a biological tissue stored in the storage device 112 is the closest to the combination. Specifically, as in Expression (17), a distance of the combination of the quantitative values is calculated and the types of tissues with the shortest distance to the pixel is obtained. Then, serial numbers assigned to the plurality of types of biological tissues are output as the intermediate information values F.

$$F = \operatorname*{argmin}_{i}(\|X - X_i\|), \quad (17)$$

$$\|X - X_i\| = (T1 - T1_i)^2 + (T2 - T2_i)^2 + (PD - PD_i)^2$$

Here, in Expression (17), is a number indicating a kind of biological tissue and $t1_i$, $T2_i$, and $PD_i$ are representative quantitative values of biological tissues.

In Expression (17), an Euclid distance is used. However, by obtaining a variance of the quantitative values of each biological tissue and calculating a Mahalanobis distance, it is also possible to obtain the kind of tissue with the shortest distance to the pixel.

The advantageous effect of outputting the discrete intermediate information values in the variable conversion unit 220 as in the modification example will be described. By using the discrete intermediate information values, it is possible to classify pixels discretely and then generate a diagnosis image in regard to specific classification on the basis of another index. Thus, it is possible to improve efficiency of a diagnosis work of the user. For example, the numbers for the kinds of biological tissues are used as the intermediate information values, and the image generation input variable selection unit 231 stores the numbers (the intermediate information values) for the kinds of the biological tissues and the diffusion coefficients (the quantitative values) in the storage device 112 so that the numbers and the diffusion coefficients can be selected. When the pixel value setting function is defined so that a part in which a kind of biological tissue is gray matter and a diffusion coefficient is large is displayed as a diagnosis image, a diagnosis image in which a tumor is weighted in the gray matter can be obtained. Further, in the second embodiment, since the distributions of the input variables (the intermediate information values and the quantitative values) are displayed by the image generation input variable display unit 232, the state of a part weighted in a diagnosis image can be numerically confirmed based on an image indicating the distributions of the input variables. For example, in a case in which a weighted image in which a tumor of gray matter is suspicious can be obtained, a diagnostician can see the distributions of the diffusion coefficients or the like of the gray matter displayed by the image generation input variable display unit and can confirm whether the suspicious tumor is really a tumor.

Modification Example 5 of Second Embodiment

In the second embodiment, the configuration in which the image generation input variable display unit 232 displays the simultaneous distribution of two or more input variables (the intermediate information values or the intermediate information value and the quantitative value) as in the region S402 of FIG. 4 has been described. The distributions of the individual intermediate information values or quantitative values may displayed. Specifically, for example, a box-and-whisker plot indicating a distribution of each input variable (the intermediate information values and the quantitative values) can be displayed as in an image generation input variable display region 501 illustrated in FIG. 8. In the box-and-whisker plot, each median value and each interquartile range may be displayed. In the bar graph, characteristics of the distribution may be displayed with a figure indicating an error bar. In this way, by displaying the distributions of the individual input variables, there is an advantage that person comparing and seeing the simultaneous distribution can easily understand a change in a numerical value. Accordingly, for example, in a case in which a doctor explains to a patient, it is better to use the distributions of the individual input variables so that the patient can easily understand the numerical values.

Modification Example 6 of Second Embodiment

In the foregoing Modification Example 4, in a case in which the image generation input variable selection unit 231 selects one discrete variable and one continuous variable, the image generation input variable display unit 232 may classify the pixels according to the discrete value (the type of biological tissue) and display a distribution of a continuous value in each classification as in FIG. 9 instead of the display region 402 of FIG. 4. For example, in a case in which the image generation input variable selection unit 231 selects the serial number of the kind of biological tissue as the discrete variable and selects the diffusion coefficient D which is a quantitative value as the continuous variable, a display region 601 illustrated in FIG. 9 is displayed. In the example of FIG. 9, the pixels can be allocated to the serial numbers of the kinds of biological tissues and names of the kinds of biological tissues Fat, WM, GM, and CSF are allocated for display. The diffusion coefficients are known to have distributions inherent to the biological tissues. Therefore, in a case in which the diffusion coefficient of a specific tissue is abnormal in the display of FIG. 9, it is possible to easily determine that abnormality such as cerebral infarction occurs and which tissue is abnormal. In this way, in a case in which the discrete variable and the continuous variable are selected, there is the advantage that it is easy to make diagnosis by classifying and displaying the pixels with the discrete variable.

Modification Example 7 of Second Embodiment

In the second embodiment, the configuration in which the image generation input variable display unit 232 displays the simultaneous distribution of two or more input variables (the intermediate information values or the intermediate information value and the quantitative value) as in the region S402 of FIG. 4 has been described. In addition to this configuration, pixel values of a diagnosis image generated by the diagnosis image calculation unit 223 may be plotted in a 2-dimensional space of the input variable. Thus, it is possible to confirm which region of the input variable is weighted to generate the diagnosis image, and thus there is the advantage that it is easy to understand relevance between the diagnosis image and the intermediate information.

Modification Example 8 of Second Embodiment

In the second embodiment, the quantitative value reception unit 210 may perform a process of applying a space filter such as a Gaussian filter when the quantitative data is received. Thus, the diagnosis image spatially smooth and intermediate information value can be obtained, and thus the quality of the diagnosis image is improved. The space filter may be a filter that weights a local change of the quantitative value as in a differential filter. Thus, the intermediate information and the diagnosis image in which the local change is weighted can be obtained, and thus diagnosability is improved.

Third Embodiment

Next, a third embodiment of the invention will be described. In the third embodiment, an MRI apparatus has basically the same configuration as the MRI apparatus according to the second embodiment, but has a function of allowing a user to adjust a pixel value setting function and parameters of the pixel value setting function used by the diagnosis image calculation unit 233 unlike the second embodiment.

Specifically, the diagnosis image generation unit 230 according to the embodiment further includes a pixel value setting function adjustment unit 701, as illustrated in FIG. 10, in addition to the image generation input variable selection unit 231, the image generation input variable display unit 232, and the diagnosis image calculation unit 233. In response to an operation by the user, the pixel value setting function adjustment unit 701 changes the pixel value setting function used when the diagnosis image calculation unit 233 allocates the pixel value for each pixel in accordance with the combination of the values of the input variables (the combination of two or more intermediate information values or the combination of the intermediate information value and the quantitative value). Thus, the pixel value allocated to the pixel is adjusted.

FIG. 11 illustrates a processing flow of the medical image diagnosis supporting unit 200 according to the third embodiment. In the processing flow of FIG. 11, steps S301 to S304 are the same as the steps of the flow of FIG. 7 according to the second embodiment. The quantitative values are received, the intermediate information values F1 and F2 are calculated, and the intermediate information values F1 and F2 are displayed. Subsequently, the pixel value setting function adjustment unit 701 displays a user interface to receive adjustment of a pixel value from the user as in FIG. 12 in step S801. When an operation of adjusting the pixel value is received from the user, the pixel value setting function used by the diagnosis image calculation unit 233 is changed (step S801). Subsequently, in step S305, the diagnosis image calculation unit 233 sets the pixel value for each pixel according to the input variable using the pixel value setting function adjusted in step S801 and generates and displays the diagnosis image (step S306).

FIG. 12 illustrates an example of a screen 900 for the user interface displayed on the display device 111 by the pixel value setting function adjustment unit 701. The screen of FIG. 12 further includes an adjustment reception region 901 in addition to the quantitative value reading instruction reception region 401, the input variable display region 402, and the diagnosis image display region 403 as in FIG. 4. The adjustment reception region 901 includes a parameter adjustment reception region 902 and an adjustment completion instruction reception region 903. When the user sees a 2-dimensional distribution (simultaneous distribution) of the input variables in the region 402 displayed in step S304 and desires to adjust the pixel value, the user adjusts a constant of the function in the parameter adjustment reception region 902 through the input device 116. The pixel value setting function adjustment unit 701 changes the parameter of the pixel value setting function stored in the storage device 112 to a value received in the region 902. When the user operates (clicks) the adjustment completion instruction reception region 903 through the input device 116, step S801 for adjusting the pixel value setting function ends.

Hereinafter, the pixel value setting function adjustment unit 701 according to the embodiment will be described in more detail. Here, for example, a case will be described in which the variable conversion unit 220 outputs the intermediate information values F1 and F2 expressed in Expressions (5) and (6) in the first embodiment, the image generation input variable selection unit 241 selects F1 and F2 as input variables, and the diagnosis image calculation unit 233 sets the pixel values using the pixel value setting function expressed in Expression (13). The pixel value setting function adjustment unit 701 receives adjustment of U, V, and W which are the parameters of the function of Expression (13) in the image calculation parameter adjustment reception region 901 illustrated in FIG. 12 from the user. Specifically, slide bards corresponding to U, V, and W are displayed in the region 901. In a case in which the user slides the positions of the bars through the input device 116, the pixel value setting function adjustment unit 701 changes the values of U, V, and N according to the slide amounts and stores the changed parameters in the storage device 112. Thus, for example, the user can set a value close to F1 of a tissue desired to be weighted as U, set a value close to F2 of the tissue desired to be weighted as V, and adjust a value of a radius of a range of F1 and F2 of the weighted tissue as W. Subsequently, when the user clicks a button of the image calculation adjustment end reception region 902 to input an end instruction, the diagnosis image calculation unit 233 calculates the pixel value G of each pixel by substituting F1 and F2 to Expression (13) in which the parameters U, V, and N are adjusted.

In the configuration, for example, when the user inputs values close to F1 and F2 of an abnormal part as U and V in the region 902, a diagnosis image in which the abnormal part is weighted can be obtained. Accordingly, a preferred diagnosis image can be easily obtained while the user confirms the intermediate information values in the region 402. Since many quantitative values are converted into a small number of kinds of intermediate information to be displayed, the user can easily adjust the values compared to a case in which the function is directly applied to the quantitative values.

As described above, according to the embodiment, it is possible to generate the diagnosis image according to the preference of the user and an improvement in operability and diagnosability can be expected.

The flow may be changed the process returns to step S801 again and the pixel value setting function can be adjusted after the diagnosis image is displayed in the region 403 of FIG. 12 in step S306. In this case, since the user can see the diagnosis image displayed in the region 403 and adjust the pixel value setting function, it is possible to generate the diagnosis image in which a desired tissue (part) is more weighted.

In the embodiment, when the image generation input variable display unit 232 generates the image in which the distributions of the input variables (the intermediate information values and the like) are displayed, the range of the values of the input variables used to generate the image in which the distributions are displayed may not be set from the minimum value to the maximum value of the input variables or the image may be generated using only a part of the range. For example, a distribution domain designation reception portion (not illustrated) in which a range of values in which the user desires to display the distribution can be input may be formed on the screen 900 so that the range of the values of the input variables can be determined. Specifically, in the image generation input variable display region 402, a function of receiving designation of a region through clicking or dragging of a mouse from the user is added to the image generation input variable display unit 232. Then, in a case in which the pixel value setting function adjustment unit 701 receives the designation of the range of the values of the input variables on the display region 402 from the user during the adjustment in step S801, a maximum value and a minimum value of the set range are set as the range of the values of the input variables used at the time of generating an image in which the distributions of the input variables are displayed. The image generation input variable display unit 232 recalculates a histogram or the like indicating the distributions of the input variables using only the pixels which have the variable values within the ranges of the values of a distribution domain and redisplays the histogram or the like in the region 402. Thus, the distributions of the input variables (the intermediate information values or the like) of the range of the values desired by the user are displayed, and thus there is the advantage that the image calculation adjustment is easy.

Fourth Embodiment

Next, a fourth embodiment of the invention will be described. In the fourth embodiment, an MRI apparatus has basically the same configuration as the MRI apparatus according to the second embodiment, but has a function of allowing a user to adjust the parameters of the variable conversion function obtained by the function calculation unit 221 or the variable conversion function stored in advance in the storage device 112 unlike the second embodiment.

Specifically, the variable conversion unit 220 further includes a variable conversion function adjustment unit 1001 illustrated in FIG. 13 in addition to the function calculation unit 221. In response to an operation by the user, the variable conversion function adjustment unit 1001 changes the variable conversion function obtained by the function calculation unit 221 or the variable conversion function stored in advance in the storage device 112. Thus, the intermediate information values calculated using the variable conversion function by the variable conversion unit 220 are adjusted.

FIG. 14 illustrates a processing flow of the medical image diagnosis supporting unit 200 according to the third embodiment. After the quantitative value reception unit 210 receives the quantitative values in step S301, the variable conversion function adjustment unit 1001 displays a screen 1200 for the user interface illustrated in FIG. 15 on the display device. The screen 1200 further includes a variable conversion adjustment reception region 1201 in addition to the quantitative value reading instruction reception region 401, the image generation input variable display region 402, and the diagnosis image display region 403. The variable conversion adjustment reception region 1201 includes a variable conversion parameter adjustment reception region 1202 and a variable conversion adjustment end reception region 1203. In the variable conversion adjustment reception region 1201, slide bars for adjusting the parameters of the variable conversion function are displayed. The user can adjust the parameters of the variable conversion function by adjusting the positions of the bars through the input device 116 (step S1101). When the user adjusts values of the parameters in the variable conversion parameter adjustment reception region 1202, the variable conversion function adjustment unit 1001 changes the parameters of the variable conversion function stored in the storage device 112. When the user operates (clicks) the variable conversion adjustment end reception region 1203 through the input device 116, the adjustment of the variable conversion function ends. The variable conversion unit 220 reads the changed variable conversion function from the storage device 112 and calculates the intermediate information values (step S302-1). Thereafter, steps S302-2 to 306 are performed as in the second embodiment.

For example, in a case in which the variable conversion unit 220 outputs the intermediate information values F1 and F2 by the variable conversion functions f1 and f2 expressed in Expressions (5) and (6) in the first embodiment, the variable conversion function adjustment unit 1001 includes slide bars to adjust conversion parameters A1, A2, B1, B2, C1, and C2 in Expressions (5) and (6) in the region 1202 as in FIG. 15. In FIG. 15, only the slide bars for adjustment of some of the conversion parameters A1, B1, and C1 are illustrated for convenience.

According to the embodiment, for example, in a case in which a lesion tissue and a normal tissue are distributed at close positions on a simultaneous distribution display screen of the region 402 in which the simultaneous distributions of the intermediate information values and the like are shown, the lesion tissue and the normal tissue can be distributed at distant positions on the simultaneous distribution display screen by adjusting the parameters of the variable conversion function. Accordingly, since the diagnosis image calculation unit 233 can easily generate, for example, an image in which the lesion tissue is weighted, it is possible to generate an image suitable as the diagnosis image of the user.

REFERENCE SIGNS LIST

2 medical image diagnosis supporting apparatus
10 region
100 MRI apparatus
101 magnet
102 gradient magnetic field coil
103 subject
104 sequencer
105 gradient magnetic field power supply
106 high-frequency magnetic field generator
107 RF coil
108 RF probe
109 receiver
110 computer
111 display device
112 storage device
113 shim coil
114 shim power supply
115 bed
116 input device
200 medical image diagnosis supporting unit
210 quantitative value reception unit
220 variable conversion unit
221 function calculation unit
230 diagnosis image calculation unit
231 image generation input variable selection unit
232 image generation input variable display unit 233 diagnosis image calculation unit
400 screen of user interface
401 quantitative value reading instruction reception region
402 image generation input variable display region
403 diagnosis image display region
501 image generate input variable display region
601 image generation input variable display region
701 diagnosis image calculation adjustment unit
900 screen for user interface
901 adjustment reception region
902 parameter adjustment reception region
903 adjustment completion instruction reception region
1001 variable conversion adjustment unit
1200 screen for user interface
1201 variable conversion adjustment reception region
1202 variable conversion parameter adjustment reception region
1203 variable conversion adjustment end reception region

The invention claimed is:

1. A medical image diagnosis supporting apparatus comprising:
   a quantitative value reception unit that receives data of two or more predetermined kinds of quantitative values obtained in advance at a plurality of points in a predetermined region of a subject;
   a variable conversion unit that calculates one or more kinds of intermediate information values which are dependent on the two or more kinds of quantitative values at each of the points using the two or more kinds of quantitative values and one or more kinds of variable conversion functions, the variable conversion unit includes a function calculation unit that obtains the one or more kinds of variable conversion functions by calculation using the two or more kinds of quantitative values at the plurality of points received by the quantitative value reception unit, wherein the function calculation unit obtains the one or more kinds of variable conversion functions by calculation so that a variance of the intermediate information values at the plurality of points increases; and
   a diagnosis image calculation unit that calculates a diagnosis image for the region,
   wherein the diagnosis image calculation unit sets a pixel value at each of the points in accordance with a combination of two or more kinds of intermediate information values obtained at each of the points by the variable conversion unit or a combination of one or more of intermediate information values and one or more kinds of quantitative values at the point and generates the diagnosis image.

2. The medical image diagnosis supporting apparatus according to claim 1,
   wherein the diagnosis image calculation unit includes a display control unit that causes a display device to display a distribution of the two or more kinds of intermediate information values or a distribution of combinations of the values, or a distribution of the one or more kinds of intermediate information values and the one or more kinds of quantitative values or a distribution of combinations of the values at the plurality of points, which are used to set the pixel value.

3. The medical image diagnosis supporting apparatus according to claim 1,
   wherein the diagnosis image calculation unit sets the pixel value so that the point at which a combination of two or more kinds of intermediate information values or a combination of values of one or more kinds of intermediate information values and one or more kinds of quantitative values is a predetermined value.

4. The medical image diagnosis supporting apparatus according to claim 1,
   wherein the diagnosis image calculation unit sets the pixel value using a pixel value setting function determined in advance in accordance with the combination of the two or more kinds of intermediate information values or the combination of one or more of intermediate information values and one or more kinds of quantitative values.

5. The medical image diagnosis supporting apparatus according to claim 1,
   wherein the function calculation unit generates a variance-covariance matrix of the quantitative values at the plurality of points, obtains principal components of the variance-covariance matrix as coefficients, and obtains a linear polynomial in which the two or more quantitative values are variable as the variable conversion function.

6. The medical image diagnosis supporting apparatus according to claim 1,
   wherein the quantitative values received by the quantitative value reception unit include at least two or more of a longitudinal relaxation time, a longitudinal relaxation rate, a transverse relaxation time, a transverse relaxation rate, a proton density, magnetic susceptibility, a diffusion coefficient, an RF radiation intensity, a flow rate, and a chemical shift of the subject estimated based on data measured using a magnetic resonance imaging apparatus.

7. The medical image diagnosis supporting apparatus according to claim 1,
   wherein the variable conversion unit performs dimension reduction by calculating intermediate information values which has less number of kinds than that of quantitative values received by the quantitative value reception unit.

8. The medical image diagnosis supporting apparatus according to claim 1, further comprising:
   a selection unit that selects a combination of two or more kinds of intermediate information values or a combination of the one or more kinds of intermediate information values and one or more kinds of quantitative values among the one or more kinds of intermediate information values calculated by the variable conversion unit and the two or more kinds of quantitative values received by the quantitative value reception unit,
   wherein the diagnosis image calculation unit sets the pixel value at each of the points in accordance with the combination of the selection unit.

9. The medical image diagnosis supporting apparatus according to claim 2,
   wherein at least one kind of intermediate information value included in the combination of the two or more kinds of intermediate information values used for the diagnosis image calculation unit to set the pixel value or at least one kind of intermediate information value included in the combination of the one or more kinds of intermediate information values and the one or more kinds of quantitative values is a discrete value, and
   wherein the display control unit causes the display device to display a distribution of intermediate information values or quantitative values different from the intermediate information values included in the combination for each discrete value of the intermediate information value.

10. The medical image diagnosis supporting apparatus according to claim 2,
wherein the distribution which the display control unit causes the display device to display is a histogram in which the number of pixels is plotted by setting the two or more kinds of intermediate information values or the one or more kinds of intermediate information values and one or more kinds of quantitative values as axes.

11. The medical image diagnosis supporting apparatus according to claim 4,
wherein the diagnosis image calculation unit includes a pixel value setting function adjustment unit that receives adjustment of a parameter of the pixel value setting function from a user.

12. The medical image diagnosis supporting apparatus according to claim 4,
wherein the variable conversion unit includes a variable conversion function adjustment unit that receives adjustment of a parameter of the variable conversion function from a user.

13. A magnetic resonance imaging apparatus comprising:
a measurement unit that obtains a nuclear magnetic resonance signal in a predetermined region of a subject;
a quantitative value image generation unit that generates two or more kinds of quantitative images having a pixel value in accordance with a quantitative value in regard to the subject in the region using the nuclear magnetic resonance signal obtained by the measurement unit;
a variable conversion unit that calculates one or more kinds of intermediate information values which are dependent on the two or more kinds of quantitative values at each of the pixels, using the quantitative value which is a pixel value of each of pixels corresponding to the two or more kinds of quantitative images and one or more variable conversion functions, the variable conversion unit includes a function calculation unit that obtains the one or more variable conversion functions by calculation using the two or more kinds of quantitative values at each of the pixels, wherein the function calculation unit obtains the one or more variable conversion functions by calculation so that a variance of the intermediate information values at the pixels increases; and
a diagnosis image calculation unit that calculates a diagnosis image for the region,
wherein the diagnosis image calculation unit sets a pixel value of the diagnosis image for each pixel in accordance with a combination of two or more kinds of intermediate information values obtained at each of the pixels by the variable conversion unit or a combination of one or more of intermediate information values and one or more kinds of quantitative values at the pixel and generates the diagnosis image.

* * * * *